(12) United States Patent
Schmidt et al.

(10) Patent No.: US 8,247,234 B2
(45) Date of Patent: Aug. 21, 2012

(54) ISOTOPICALLY LABELED COMPOSITIONS AND METHOD

(75) Inventors: Jurgen G. Schmidt, Los Alamos, NM (US); David B. Kimball, Los Alamos, NM (US); Marc A. Alvarez, Santa Fe, NM (US); Robert F. Williams, Los Alamos, NM (US); Rudolfo A. Martinez, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 13/151,755

(22) Filed: Jun. 2, 2011

(65) Prior Publication Data

US 2011/0269985 A1    Nov. 3, 2011

Related U.S. Application Data

(62) Division of application No. 11/818,984, filed on Jun. 15, 2007, now Pat. No. 7,977,102.

(51) Int. Cl.
*G01N 33/00* (2006.01)
(52) U.S. Cl. ............................. 436/56; 436/57; 436/177
(58) Field of Classification Search .................... 436/56, 436/57, 177
See application file for complete search history.

(56) References Cited

U.S. PATENT DOCUMENTS
7,288,382 B2 * 10/2007 Harbury et al. ................. 435/7.1
* cited by examiner

*Primary Examiner* — Sam P Siefke
(74) *Attorney, Agent, or Firm* — Samuel L. Borkowsky

(57) ABSTRACT

Compounds having stable isotopes $^{13}$C and/or $^{2}$H were synthesized from precursor compositions having solid phase supports or affinity tags.

7 Claims, No Drawings

ISOTOPICALLY LABELED COMPOSITIONS AND METHOD

RELATED APPLICATIONS

This application is a divisional of U.S. nonprovisional application Ser. No. 11/818,984 entitled "Isotopically Labeled Compositions and Method," filed Jun. 15, 2007, now allowed, incorporated by reference herein.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to compositions and methods for synthesizing compounds labeled with stable isotopes.

BACKGROUND OF THE INVENTION

Isotopically labeled molecules are used for structural and mechanistic studies of important chemical and biological processes. Isotopically labeled amino acids and nucleotides, for example, are used for structural and mechanistic studies of proteins and oligonucleotides. Isotopically labeled biologically active compounds, for example, are used for many phases of drug discovery and development including elucidation of biosynthetic pathways, pharmacokinetics, and drug metabolism. Compounds can be isotopically enriched with a radioactive label or with a nonradioactive label. Non-radioactive isotopes (i.e. stable isotopes) can be used to avoid subsequent disposal of radioactive waste.

Compounds labeled with stable isotopes such as carbon-13 ($^{13}C$) and deuterium ($^2H$) typically are synthesized using solution-based methods (see, for example: U.S. Pat. No. 6,730,805 to Martinez et al. entitled "Synthesis of $^2H$—and $^{13}C$-Substituted Compounds"; U.S. Pat. No. 6,541,671 to Martinez et al. entitled "Synthesis of [$^2H_1$, $^{13}C$], [$^2H_2$, $^{13}C$] and [$^2H_3$, $^{13}C$]Methyl Aryl Sulfides"; U.S. Pat. No. 6,713,044 to Martinez entitled "Synthesis of [$^2H_1$, $^{13}C$], [$^2H_2$, $^{13}C$} and [$^2H_3$, $^{13}C$]Methyl Aryl Sulfides"; U.S. Pat. No. 6,764,673 to Martinez et al. entitled "Synthesis of [$^2H_1$, $^{13}C$], [$^2H_2$, $^{13}C$] and [$^2H_3$, $^{13}C$]Methyl Aryl Sulfones and Sulfoxides"; U.S. Pat. No. 6,764,673; and U.S. Pat. No. 6,753,446 to Martinez et al. entitled "Synthesis of Labeled Oxalic Acid Derivatives," all incorporated by reference herein).

Typical solution phase methods often result in product mixtures that decrease the overall yield of a desired isotopically labeled material. In addition, laborious separation and purification steps may also be needed to isolate the desired labeled material and these steps add to the cost and inefficiency of a synthesis of a desired isotopically labeled material.

The remains a need for better methods for synthesizing isotopically labeled compounds, and for compositions that can be easily converted to isotopically labeled compounds.

SUMMARY OF THE INVENTION

In accordance with the purposes of the present invention, as embodied and broadly described herein, the present invention includes a composition having the formula

A-D-E-C(TXZ)

wherein A includes a support or an affinity tag;

wherein D includes an aryl group;

wherein E includes a group chosen from sulfur, sulfoxide, sulfone, selenium, selenoxide, and selenone;

wherein T, X, and Z include groups each independently chosen from $^1H$, $^2H$, a $C_1$-$C_4$ alkyl, fluoro, chloro, bromo, iodo, amino, $NHR$, $NR_2$, and $OR$;

wherein R includes a group chosen from a $C_1$-$C_4$ alkyl, chloro, bromo, amino, monocyclic aryl, substituted monocyclic aryl, bicyclic aryl, and substituted bicyclic aryl; and wherein at least one of C, T, X, and Z groups includes a stable isotope, wherein the stable isotope of C is $^{13}C$ and wherein the stable isotope of T, X, Z is chosen from $^{13}C$ and $^2H$.

The invention also includes a composition having the formula

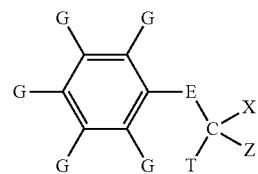

or of the formula

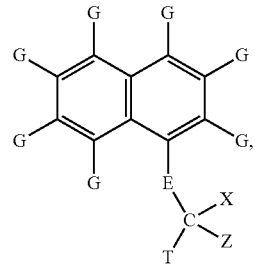

or of the formula

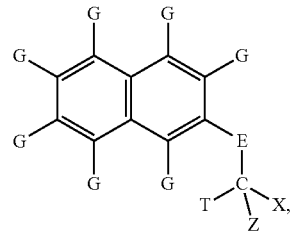

or of the formula

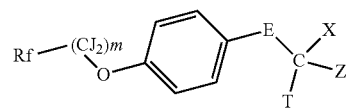

wherein each G group is independently chosen from a support, hydrogen, a $C_1$-$C_4$ alkyl, haloalkyl, cycloalkyl, cyano, fluoro, chloro, bromo, iodo, $NH_2$, $NHR$, $NR_2$, —OM, OR, and —COOQ;

wherein at least one G group is a support;

wherein M is chosen from hydrogen, alkyl, haloalkyl, cycloalkyl, phenyl, and substituted phenyl;

wherein Q is chosen from hydrogen and alkyl;

wherein E comprises a group chosen from sulfur, sulfoxide, sulfone, selenium, selenoxide, and selenone;

wherein T, X, and Z are groups each independently chosen from $^1H$, $^2H$, a $C_1$-$C_4$ alkyl, fluoro, chloro, bromo, iodo, amino, NHR, $NR_2$, and OR;

wherein R is chosen from a $C_1$-$C_4$ alkyl, chloro, bromo, amino, a monocyclic aryl, substituted monocyclic aryl, bicyclic aryl, and substituted bicyclic aryl;

wherein $R_f$ is a fluorous group;

wherein each J is independently selected from hydrogen and alkyl, wherein m is 2, 3, 4, 5, or 6; and wherein at least one of C, T, X, and Z comprises a stable isotope, wherein the stable isotope of C is $^{13}C$ and wherein the stable isotope of T, X, Z comprises $^{13}C$ or $^2H$.

The invention also includes a method for synthesizing an isotopically enriched compound. The method involves forming a composition having the formula

A-D-E-C(TXZ)

wherein A includes a support or affinity tag; wherein D includes an aryl group; wherein E includes a group chosen from sulfur, sulfoxide, sulfone, selenium, selenoxide, and selenone; wherein T, X, and Z include groups each independently chosen from $^1H$, $^2H$, a $C_1$-$C_4$ alkyl, fluoro, chloro, bromo, iodo, amino, NHR, $NR_2$, and OR; wherein R includes a group chosen from a $C_1$-$C_4$ alkyl, chloro, bromo, amino, monocyclic aryl, substituted monocyclic aryl, bicyclic aryl, and substituted bicyclic aryl; wherein at least one of C, T, X, and Z groups comprises a stable isotope, wherein the stable isotope of C is $^{13}C$, wherein the stable isotope of T, X, Z is chosen from $^{13}C$ or $^2H$;

and subjecting the composition to conditions whereby —C(TXZ) detaches from E and becomes part of an isotopically labeled compound.

DETAILED DESCRIPTION

An aspect of the invention is concerned with compositions having a solid phase support that are useful for synthesizing compounds that are isotopically labeled with $^{13}C$, $^2H$, or both $^{13}C$ and $^2H$.

Another aspect of the invention is concerned with synthesizing isotopically labeled compounds from compositions having a solid phase support. Separation and purification steps are minimized when a solid phase support is used because the desired isotopically labeled product tends to be a single labeled compound rather than a mixture of labeled compounds. In addition, the yield of the desired isotopically labeled compound tends to be at least as good as, and sometimes better than, the yield obtained when a solution-based method is used to synthesize the same isotopically labeled compound.

In some embodiments, a precursor for making an isotopically labeled compound was prepared by reacting a thiophenol resin with an excess of isotopically labeled reagent; the excess drove the reaction to completion. During the reaction, an isotopically labeled portion from the reagent became attached to the resin. This precursor can be further modified by appropriate chemical reactions before detachment from the resin, yielding the desired isotopically labeled compound and a resin byproduct that can be recovered and reused. Excess amounts of isotopically labeled reagent can also be recovered relatively easily when the work-up involves only filtration of the product resin and removal of solvents.

Other aspects of the invention are concerned with isotopically labeled compositions having affinity tags, and with the preparation of isotopically labeled compounds from these compositions. Affinity tags include fluorous groups (—$C_8F_{17}$, for example) that facilitate purification through a separation technique known in the art as fluorous solid phase extraction (see, for example: Zhang et al., "Synthetic Applications of Fluorous Solid-Phase Extraction (F-SPE)," Tetrahedron, vol. 62 (2006), pp. 11837-11865, incorporated by reference herein).

The term "fluorous" refers generally to an organic molecule, or portion of a molecule, or group that is rich in carbon-fluorine bonds. A fluorohydrocarbon is an organic compound in which at least one hydrogen atom bonded to a carbon atom has been replaced with a fluorine atom. A few examples of suitable fluorous groups for use in the present invention include, but are not limited to, —$C_4F_9$, —$C_6F_{13}$, —$C_8F_{17}$, —$C_{10}F_{21}$, —$C(CF_3)_2C_3F_7$, —$C_4F_8CF(CF_3)_2$, and —$CF_2CF_2OCF_2CF_2OCF_3$.

An embodiment of fluorous solid phase extraction (F-SPE) referred to in the art as "standard F-SPE" employs fluorous silica gel, which is made of silica gel bonded to a fluorocarbon phase such as —$Si(CH_3)_2(CH_2)_2C_8F_{17}$. This material is commercially available from FLUOROUS TECHNOLOGIES, INC. under the trade name of FLUOROFLASH®. Briefly, a crude reaction mixture containing both fluorous and non-fluorous reaction components is charged onto fluorous silica gel and then the fluorous silica gel is eluted with a fluorophobic solvent such as 70-80 percent methanol:$H_2O$, 50-60 percent $CH_3CN$:$H_2O$, 80-90 percent DMF:$H_2O$, or 100 percent DMSO. In this fluorophobic pass, non-fluorous organic compounds typically move at or near the solvent front and elute first, while fluorous compounds are retained on the fluorous silica gel. In the subsequent fluorophilic pass, elution with one of many organic solvents such as water-free methanol or acetonitrile, tetrahydrofuran, among others, then provides a fluorous fraction containing those compounds bearing the fluorous tag.

Alternatively, the philicities of the solid phase and the liquid phase may be reversed, wherein standard silica gel is used as the polar solid phase while blends of fluorous and organic solvents are used as the fluorophilic liquid phase. This alternate separation is sometimes referred to as "reverse F-SPE".

The progress of a synthesis of an isotopically labeled compound can be monitored easily by nuclear magnetic resonance (NMR) spectroscopy. When the label is $^{13}C$, a carbon NMR spectrum of a reaction mixture may be obtained as the reaction proceeds. Analysis of the NMR spectrum provides an indication of the completeness of reaction.

In an embodiment, standard F-SPE was used to prepare an isotopically labeled composition (see EXAMPLES 15 and 16, infra).

Embodiment compositions include those of the formula

A-D-E-C(TXZ).

In the above formula, "A" symbolizes a chemical support or an affinity tag. Some non-limiting examples of chemical supports include a polyfluoroalkyl support, an aryl support, a metal support, a nanoparticle support, a magnetic bead support, a silica support, a polymer support, a resin support, a silicon support, a glass support, a ceramic support, and a core-shell material support. A non-limiting example of a metal particle is a gold particle. A non-limiting example of a resin is polystyrene. Some non-limiting examples of polymers include polystyrene, TENTAGEL®, polyethylene glycol, polyethylene glycol substituted with vinyl benzene, and resin-bound thiophenol crosslinked with divinylbenzene. A non-limiting example of a nanoparticle support is gold nanoparticles. Some non-limiting examples of magnetic bead supports include ferromagnetic beads, CoSm magnetic beads, and DYNAL® magnetic beads. Magnetic bead supports may be coated with a ceramic material, such as mesoporous silica. Some non-limiting examples of glass supports include those commonly used in the synthesis of DNA. Glass beads may or may not be derivatised with other materials. Some non-limiting examples of ceramic supports include supports of silica or alumina. Some non-limiting examples of core-shell materials are gold nanoparticles of the type disclosed in U.S. Patent Application 20050025969 entitled "Gold-Coated Nanoparticles for Use in Biomedical Applications," incorporated by reference herein. Some non-limiting examples of affinity tags include those of the formula $C_6F_{13}(CH_2)_3-$, $C_8F_{17}(CH_2)_3-$, $C_8F_{17}(CH_2)_2C(CH_3)_2-$, and $C_{10}F_{21}(CH_2)_3-$.

In the above formula, "D" symbolizes an aryl group. It should be understood that aryl is meant to include monocyclic aromatic and polycyclic aromatic groups such as, but not limited to, monocyclic aryl, monocyclic aryloxy (para-O—$C_6H_4-$, for example), substituted monocyclic aryl, substituted monocyclic aryloxy, bicyclic aryl, bicyclic aryloxy, substituted bicyclic aryl, and substituted bicyclic aryloxy. In some embodiments, when aryl is monocyclic aryloxy or bicyclic aryloxy, group A may be connected to group D by oxygen of the aryloxy group. When aryl group "D" is a six-membered aromatic ring, the substitution pattern of "A" and "E" may be ortho (i.e. 1,2-), meta (i.e. 1,3-), or para (i.e. 1,4-). Aryl group "D" may be substituted in any and all positions in the ring that are not already occupied by group "A" and group "E". Some non-limiting substituents on aryl group "D" include methyl, ethyl, propyl, isopropyl, butyl, isobutyl, t-butyl, alkenyl, chloro, bromo, haloalkyl, cycloalkyl, amino, alkylamino, dialkylamino, alkoxy, and aryloxy. Some non-limiting examples of haloalkyl substituents include chloromethyl, bromoethyl, fluoroisopropyl, and iodicyclopentyl.

In the above formula, Group "E" is a chemical group that connects aryl group "D" to —C(X)(T)(Z). Group "E" can be one or more sulfur atoms (—S—, —S—S—, —S—S—S—, for example), one or more selenium atoms (—Se—, —Se—Se—, —Se—Se—Se, for example), a sulfoxide (—S(=O)—) group, a sulfone group (—S(=O)$_2$—), a selenoxide group (—Se(=O)—) or a selenone group (—Se(=O)$_2$—). If "E" is a sulfoxide group, stereoisomerism is possible at the sulfur atom because the sulfur atom of a sulfoxide group is a chiral center.

The chemical groups symbolized by T, X, and Z can each be independently selected from $^1H$, $^2H$, a $C_1$-$C_4$ alkyl, fluoro, chloro, bromo, iodo, amino, NHR, NR$_2$, alkoxy, and aryloxy. Alkoxy is symbolized as OR where the O is oxygen and the R is a group that can be, for example, a $C_1$-$C_4$ alkyl, monocyclic aryl, substituted monocyclic aryl, bicyclic aryl, and substituted bicyclic aryl.

It should also be understood that the composition of the formula

A-D-E-C(TXZ)

must include at least one stable isotope in the "C" group and/or in at least one of the groups symbolized by T, X, and Z. In some embodiments, C is isotopically enriched with $^{13}C$ while none of T, X, and Z include an isotopically enriched isotope. In embodiments, C is not isotopically enriched with $^{13}C$ but one, two, or all three of T, X, and Z include isotopically enriched groups. In yet other embodiments, C is enriched in $^{13}C$ and one, two, or three of T, X, and Z groups are isotopically enriched in $^{13}C$ and/or $^2H$.

An embodiment composition having a support is of the formula

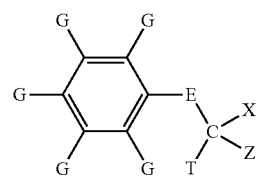

wherein each G group is independently chosen from a support, hydrogen, a $C_1$-$C_4$ alkyl, haloalkyl, cycloalkyl, cyano, fluoro, chloro, bromo, iodo, NH$_2$, NHR, NR$_2$, —OM, OR, and —COOQ. Also, at least one G group is a support, M is chosen from hydrogen, alkyl, haloalkyl, cycloalkyl, phenyl, and substituted phenyl, and Q is chosen from hydrogen and alkyl. E includes a group chosen from sulfur, sulfoxide, sulfone, selenium, selenoxide, and selenone. T, X, and Z are groups each independently chosen from $^1H$, $^2H$, a $C_1$-$C_4$ alkyl, fluoro, chloro, bromo, iodo, amino, NHR, NR$_2$, and OR. R is chosen from a $C_1$-$C_4$ alkyl, chloro, bromo, amino, a monocyclic aryl, substituted monocyclic aryl, bicyclic aryl, and substituted bicyclic aryl. At least one of C, T, X, and Z comprises a stable isotope, wherein the stable isotope of C is $^{13}C$ and wherein the stable isotope of T, X, Z is chosen from $^{13}C$ or $^2H$.

Another embodiment composition having a support is of the formula

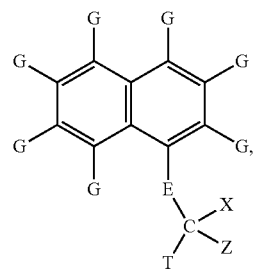

and another is its structural isomer, which is of the formula

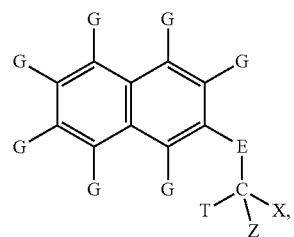

wherein each G group is independently chosen from a support, hydrogen, a $C_1$-$C_4$ alkyl, haloalkyl, cycloalkyl, cyano, fluoro, chloro, bromo, iodo, NH$_2$, NHR, NR$_2$, —OM, OR, and —COOQ. Also, at least one G group is a support, M is chosen from hydrogen, alkyl, haloalkyl, cycloalkyl, phenyl, and substituted phenyl, and Q is chosen from hydrogen and alkyl. E includes a group chosen from sulfur, sulfoxide, sulfone, selenium, selenoxide, and selenone. T, X, and Z are groups each independently chosen from $^1H$, $^2H$, a $C_1$-$C_4$ alkyl, fluoro, chloro, bromo, iodo, amino, NHR, NR$_2$, and OR. R is chosen from a $C_1$-$C_4$ alkyl, chloro, bromo, amino, a monocyclic aryl, substituted monocyclic aryl, bicyclic aryl, and substituted bicyclic aryl. At least one of C, T, X, and Z comprises a stable isotope, wherein the stable isotope of C is $^{13}C$ and wherein the stable isotope of T, X, Z is chosen from $^{13}C$ or $^2H$.

Some non-limiting embodiment sulfide-containing compositions include the following, wherein a solid phase support represented by

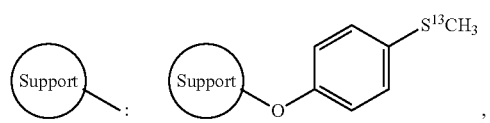

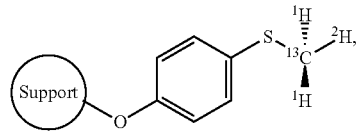

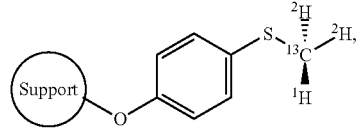

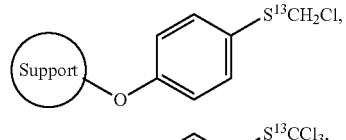

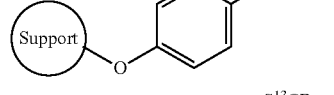

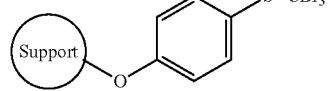

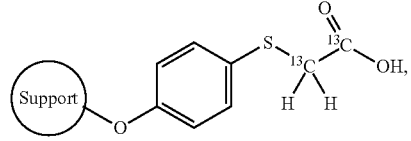

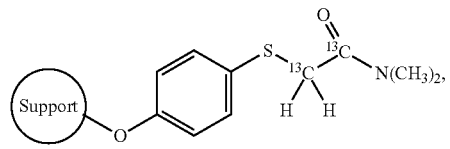

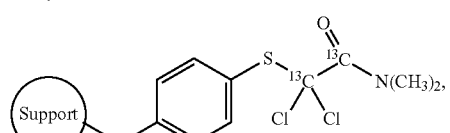

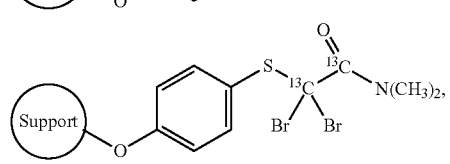

-continued

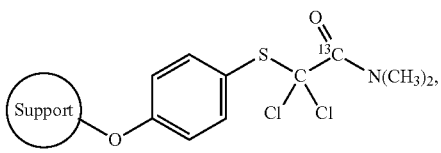

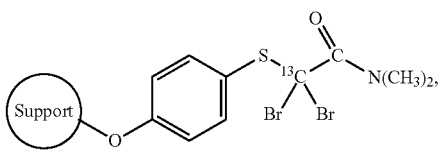

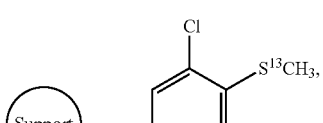

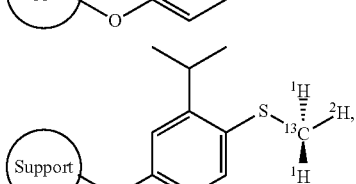

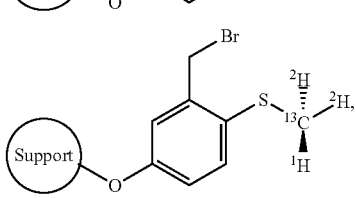

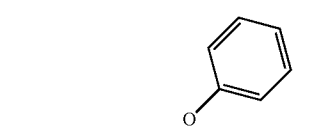

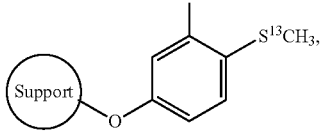

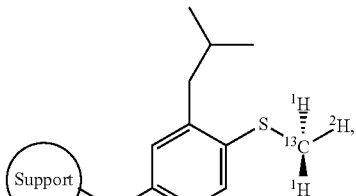

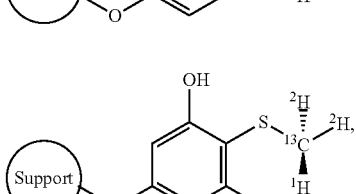

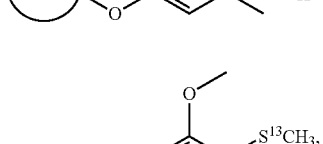

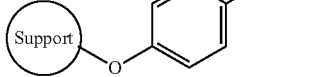

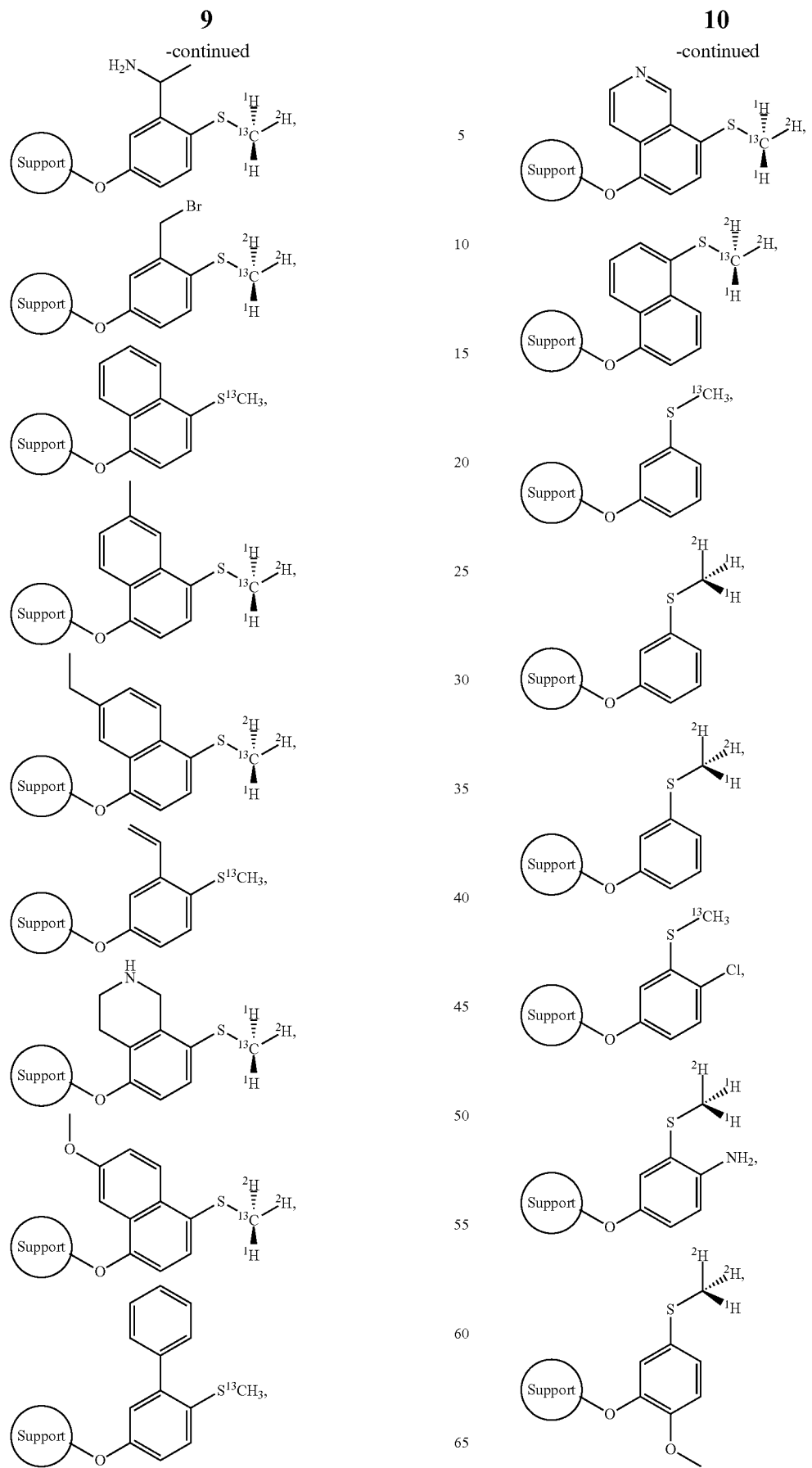

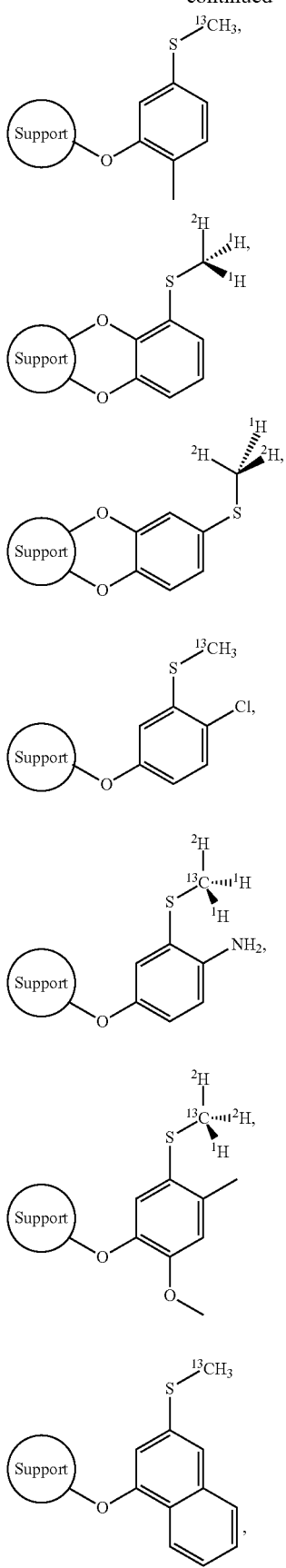
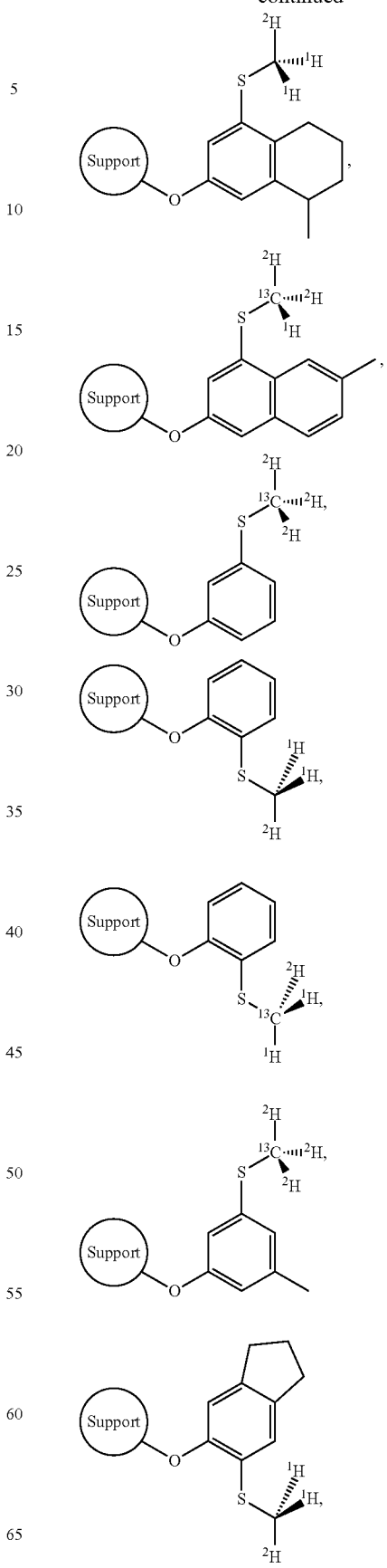

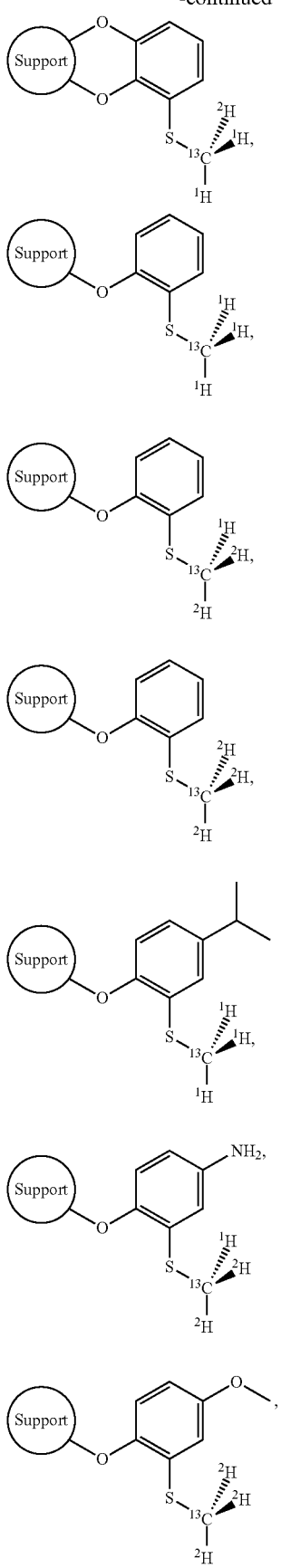

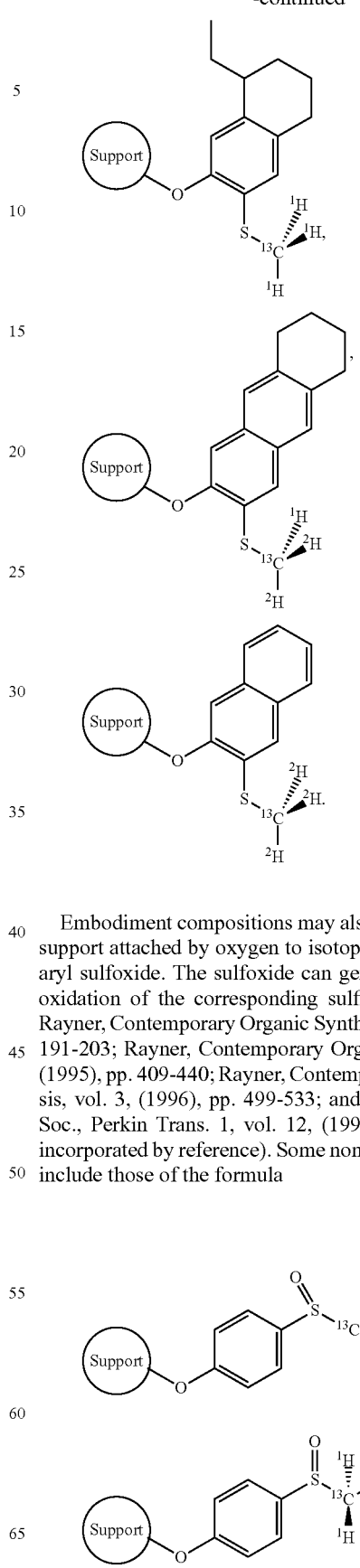

Embodiment compositions may also include a solid phase support attached by oxygen to isotopically a labeled methyl aryl sulfoxide. The sulfoxide can generally be prepared by oxidation of the corresponding sulfide (see, for example: Rayner, Contemporary Organic Synthesis, vol. 1, (1994), pp. 191-203; Rayner, Contemporary Organic Synthesis, vol. 2, (1995), pp. 409-440; Rayner, Contemporary Organic Synthesis, vol. 3, (1996), pp. 499-533; and Baird et al., J. Chem. Soc., Perkin Trans. 1, vol. 12, (1998), pp. 1973-2003, all incorporated by reference). Some non-limiting embodiments include those of the formula

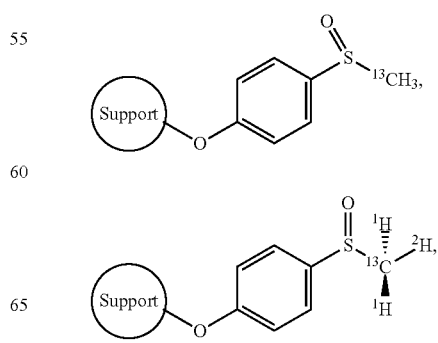

15
-continued
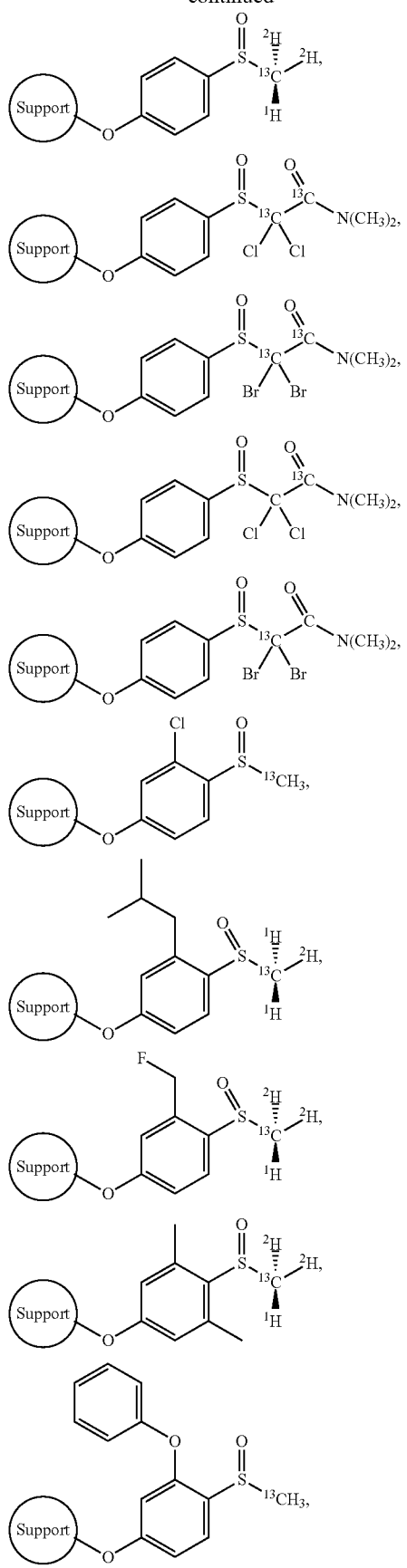
16
-continued
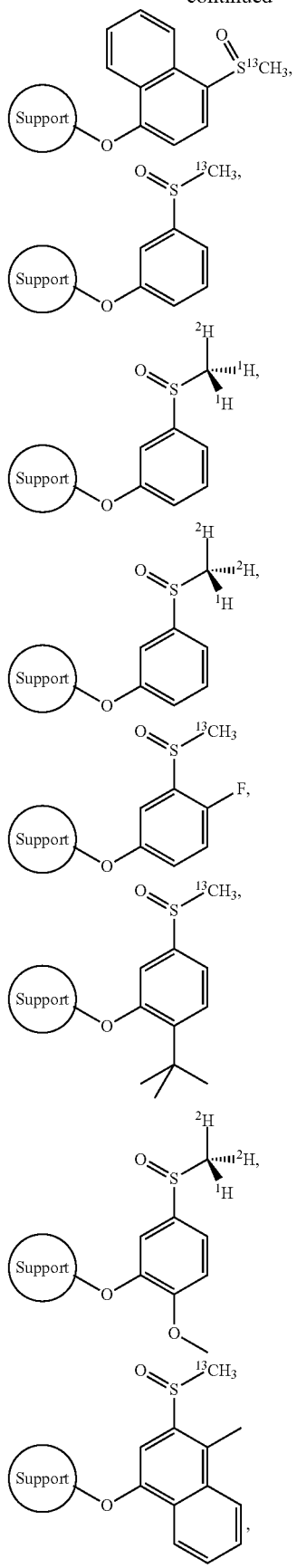

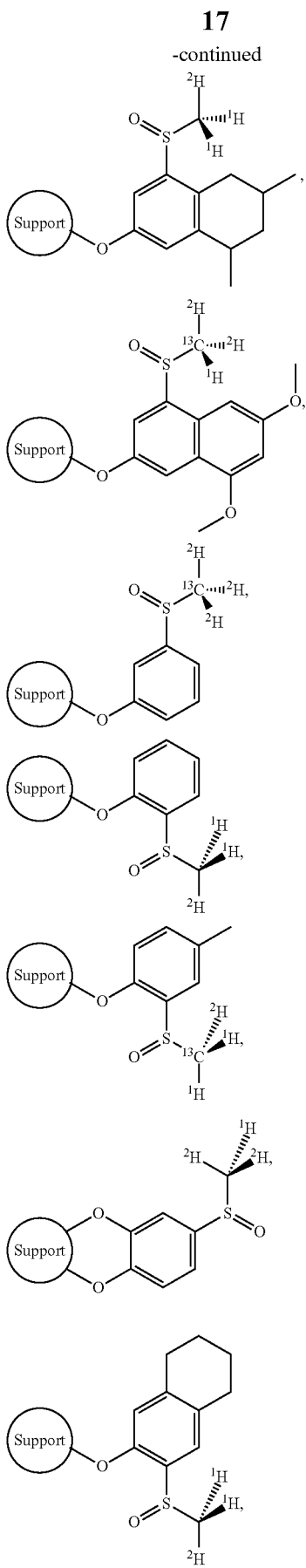
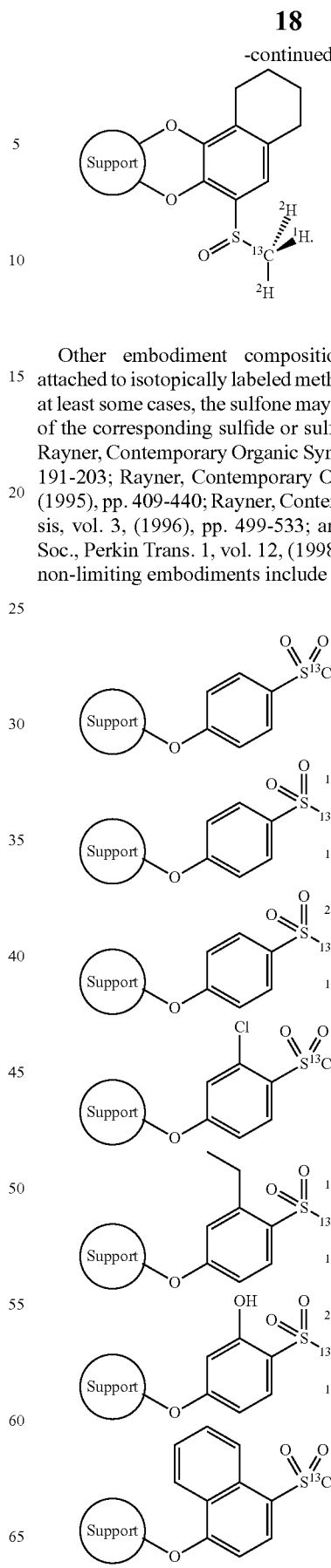

Other embodiment compositions include a support attached to isotopically labeled methyl aryl sulfone groups. In at least some cases, the sulfone may be prepared by oxidation of the corresponding sulfide or sulfoxide (see, for example: Rayner, Contemporary Organic Synthesis, vol. 1, (1994), pp. 191-203; Rayner, Contemporary Organic Synthesis, vol. 2, (1995), pp. 409-440; Rayner, Contemporary Organic Synthesis, vol. 3, (1996), pp. 499-533; and Baird et al., J. Chem. Soc., Perkin Trans. 1, vol. 12, (1998), pp. 1973-2003). Some non-limiting embodiments include those of the formula -continued
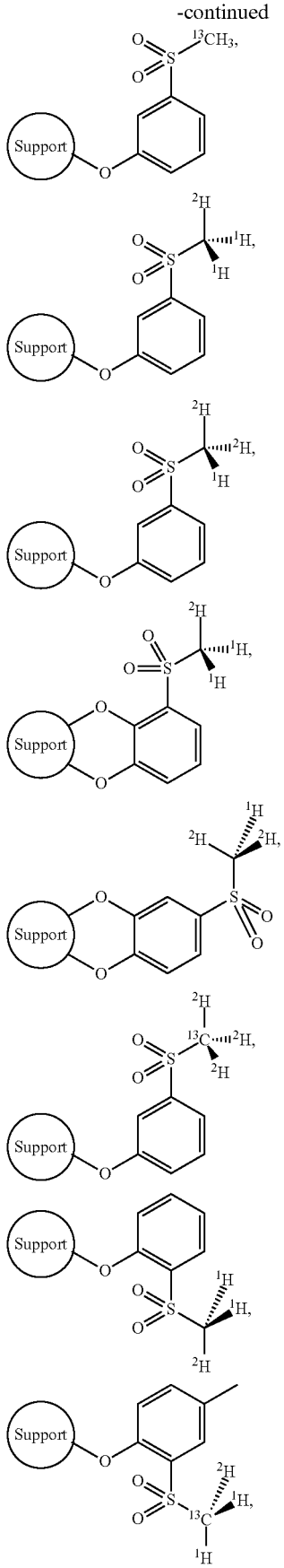
-continued
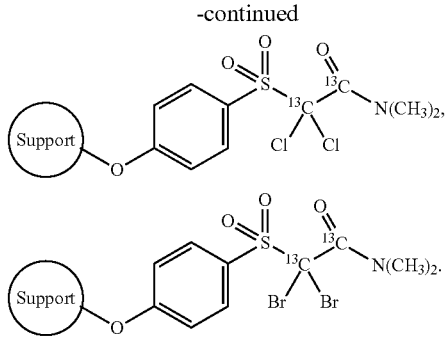
In other embodiment compositions, a solid phase support is attached to isotopically labeled methyl aryl selenide groups. Some non-limiting embodiments include those of the formula
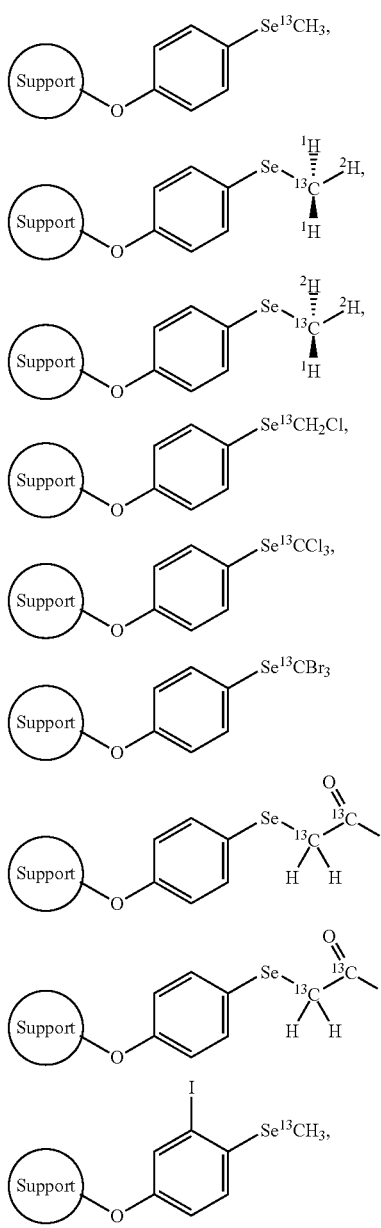

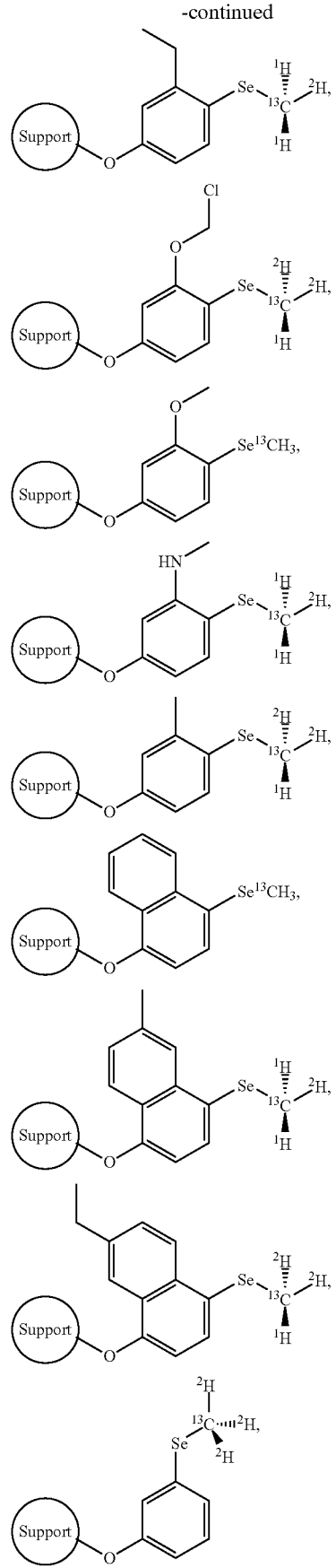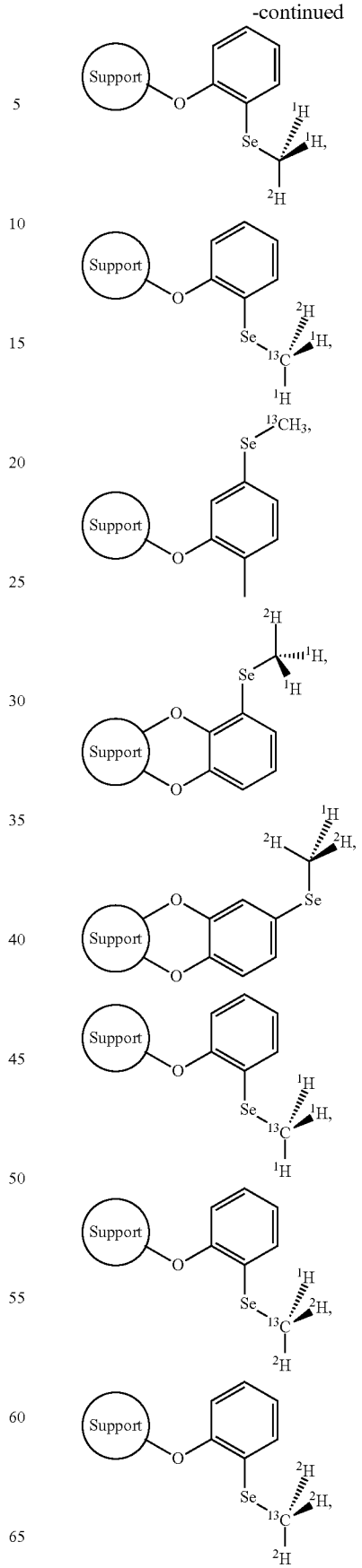

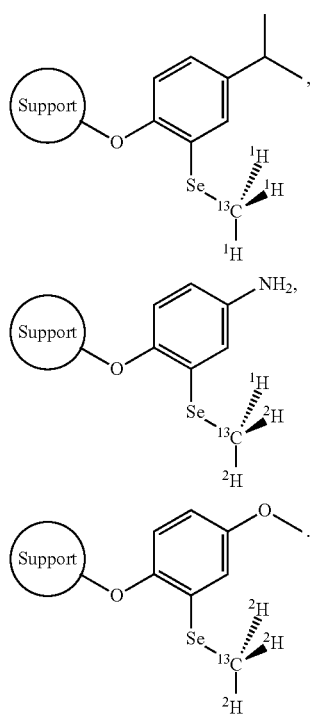
In other embodiment compositions, a solid phase support is attached to isotopically labeled methyl aryl selenoxide groups. Some non-limiting examples of this composition include those of the formula
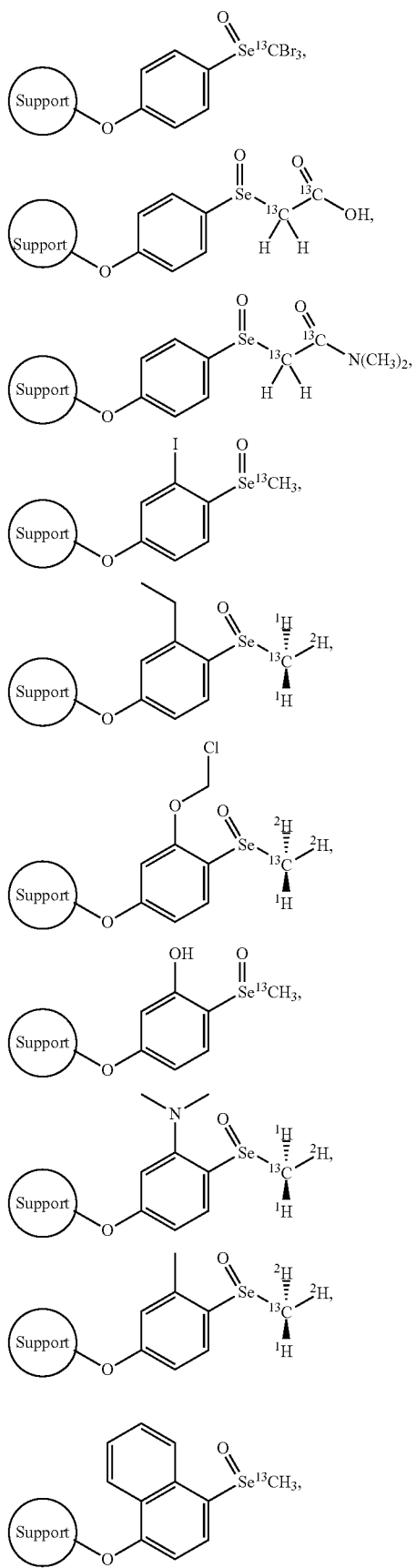

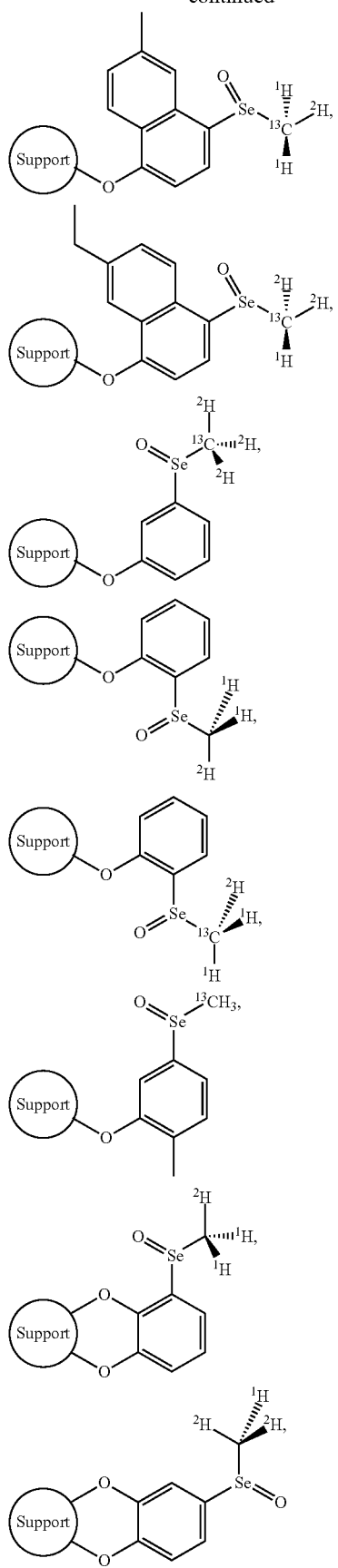
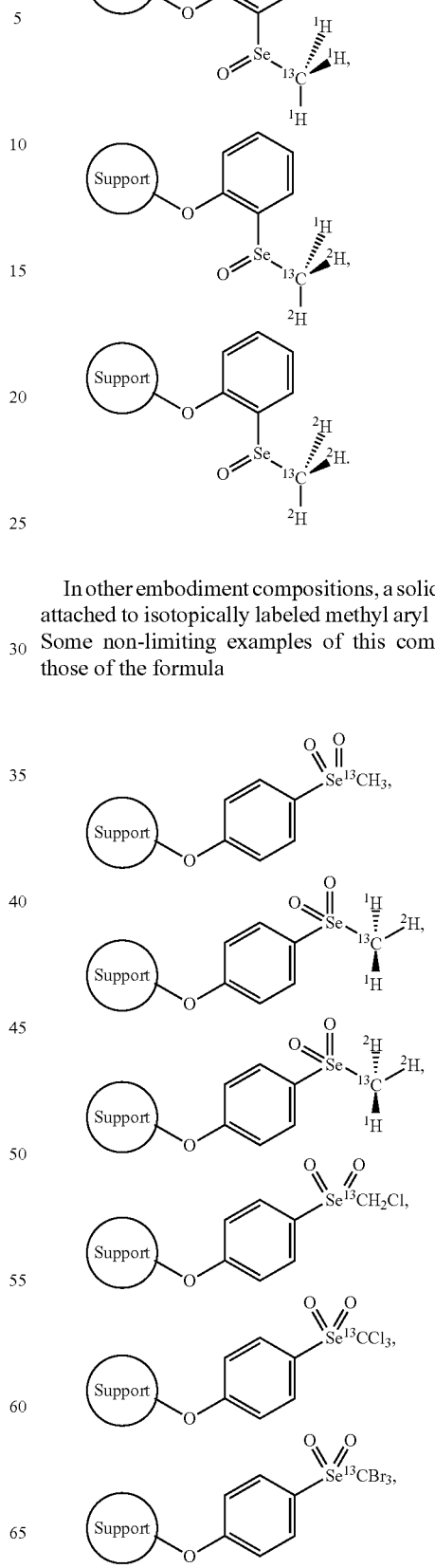
In other embodiment compositions, a solid phase support is attached to isotopically labeled methyl aryl selenone groups. Some non-limiting examples of this composition include those of the formula 27
-continued
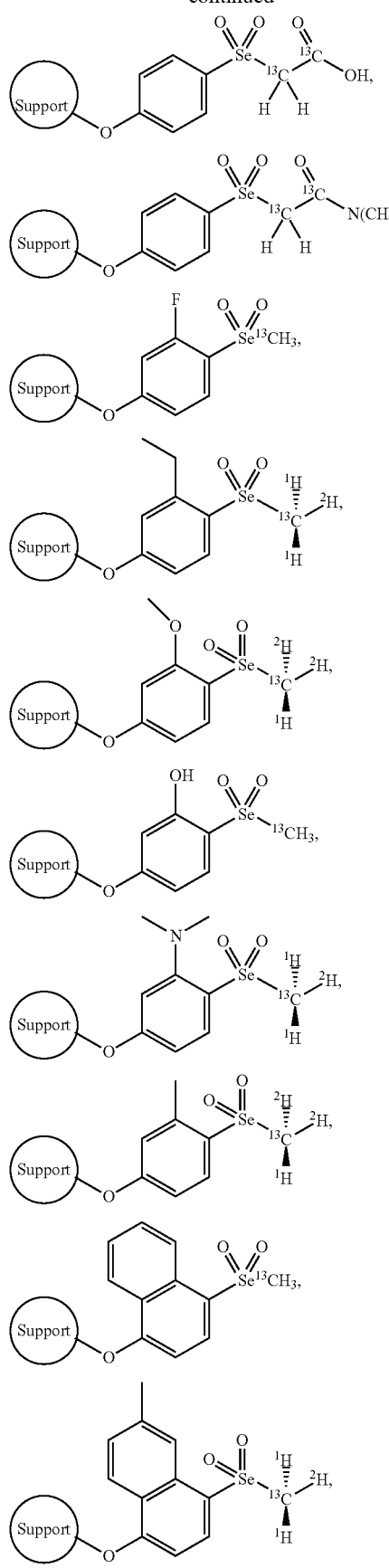
28
-continued
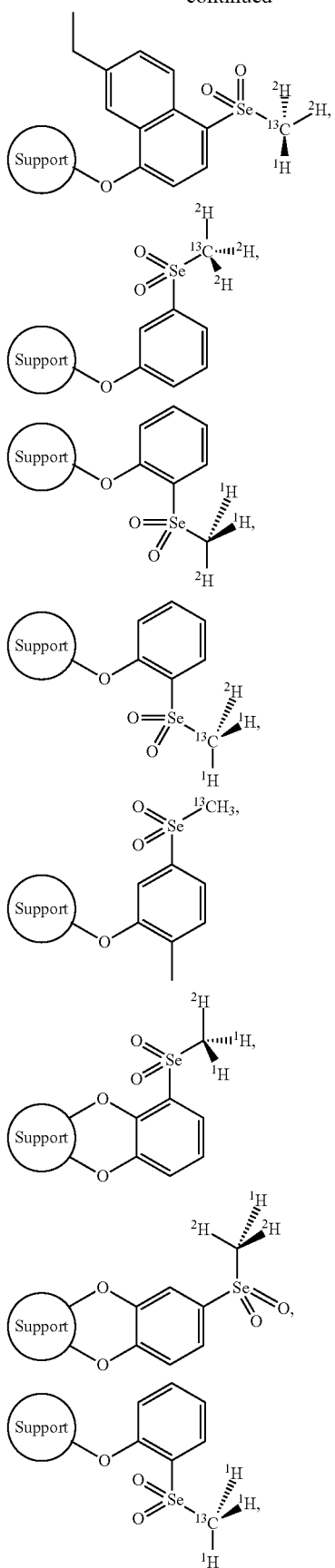

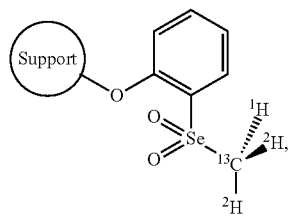
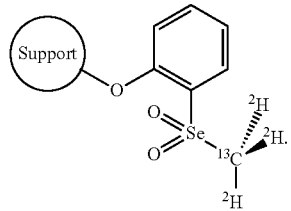
Other embodiment compositions include a solid phase support attached to isotopically labeled methyl aryl polysulfide groups. Some non-limiting examples of this composition include those of the formula
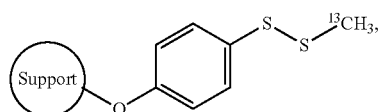
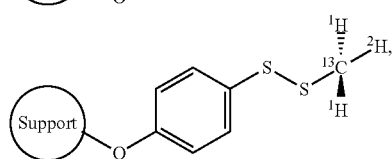
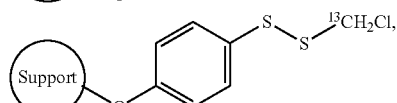
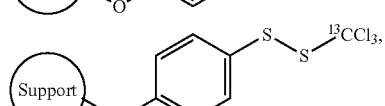
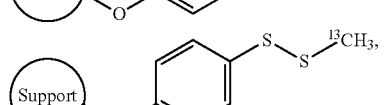
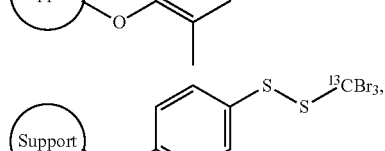
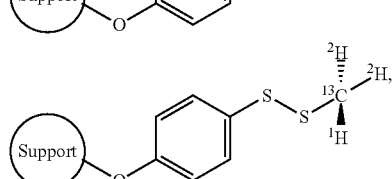
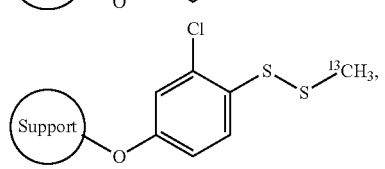
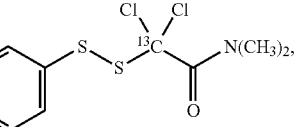
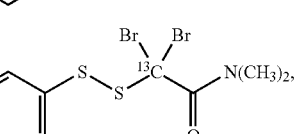
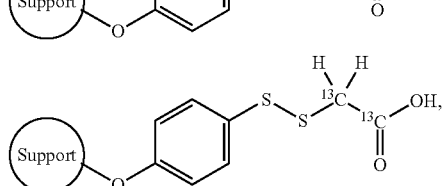
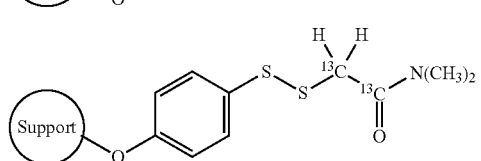
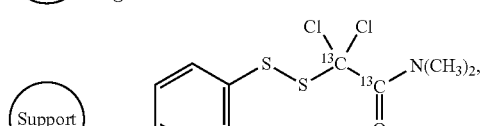
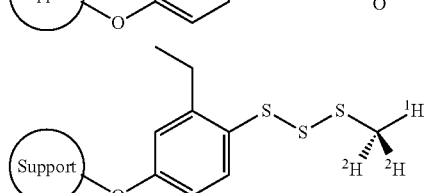
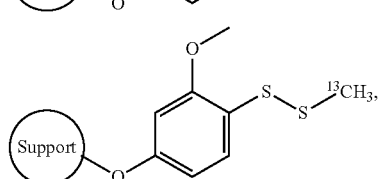
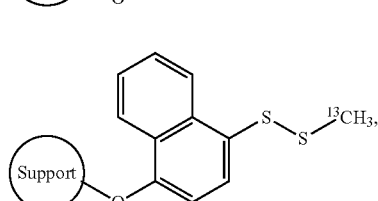
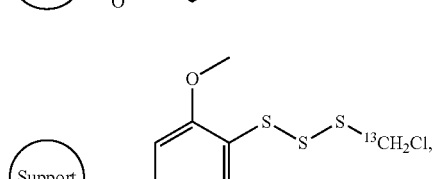
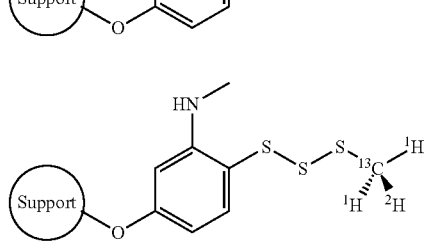

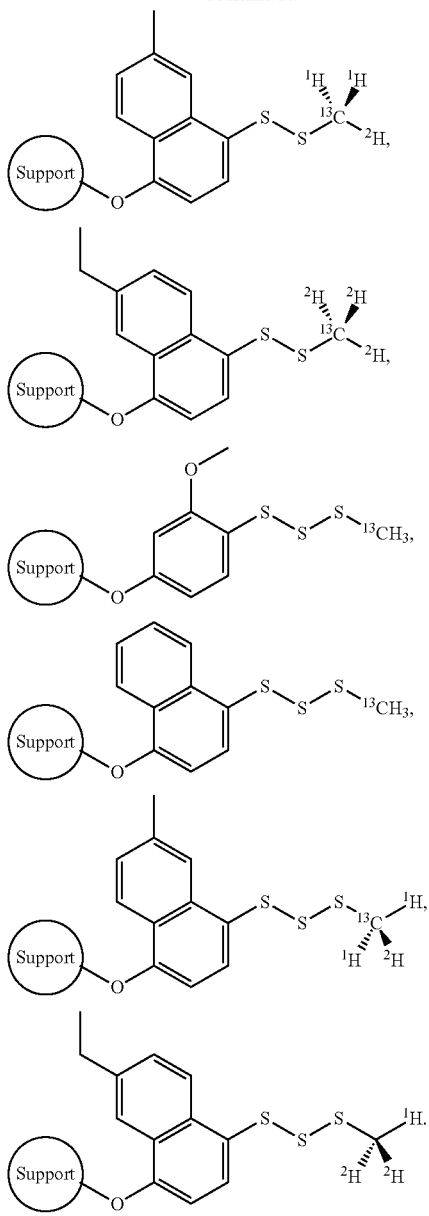

Other embodiment compositions include a solid phase support attached to isotopically labeled methyl aryl polyselenide groups. Some embodiments include those of the formula

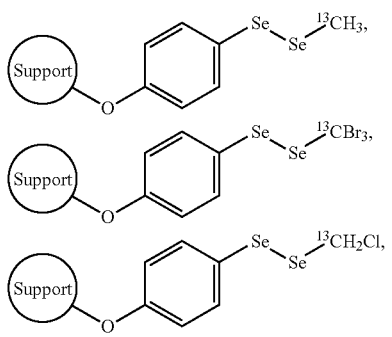

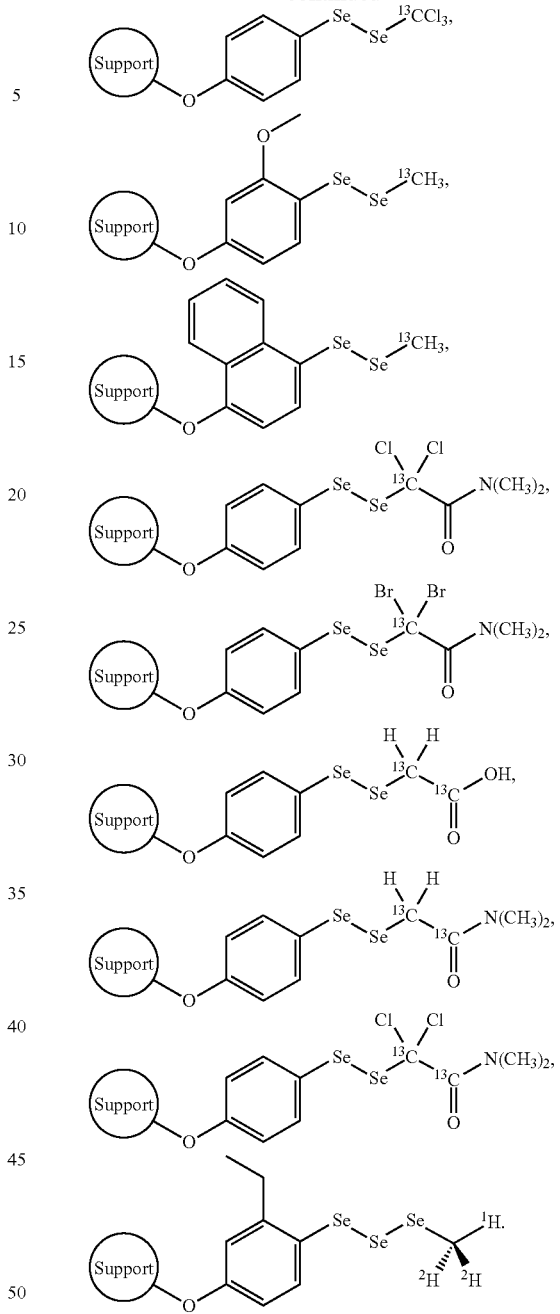

An embodiment composition that includes an affinity tag is of the formula

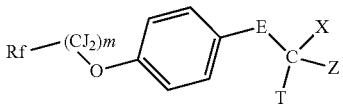

wherein T, X, and Z are groups each independently chosen from $^1H$, $^2H$, a $C_1$-$C_4$ alkyl, fluoro, chloro, bromo, iodo, amino, NHR, $NR_2$, and OR; wherein R is chosen from a $C_1$-$C_4$ alkyl, chloro, bromo, amino, a monocyclic aryl, substituted monocyclic aryl, bicyclic aryl, and substituted bicyclic aryl; wherein $R_f$ is a fluorous group; wherein each J is independently selected from hydrogen and alkyl, wherein m is 2, 3, 4, 5, or 6; wherein at least one of C, T, X, and Z comprises a stable isotope, wherein the stable isotope of C is $^{13}C$ and wherein the stable isotope of T, X, Z comprises $^{13}C$ or $^{2}H$. In the above formula, $R_f$—$(CJ_2)_m$- is exemplary of an affinity tag. Embodiment affinity tags are linear or branched fluorine-containing hydrocarbon groups. Some non-limiting affinity tag embodiments include those of the formula $C_nF_{(2n+1)}(CR_2)_m$—, or of the formula $C_nF_{(2n-1)}(CR_2)_m$—, or of the formula $C_nF_{(2n-3)}(CR_2)_m$—, where R is independently selected from hydrogen or an alkyl group, wherein n is 4, 5, 6, 7, 8, 9, 10, 11, 12, 13, 14, 15, 16, 17, or 18, and wherein m is 2, 3, 4, 5, or 6. Some non-limiting examples of alkyl groups include methyl, ethyl, propyl, isopropyl, butyl, 2-butyl, tert-butyl. Some non-limiting examples of affinity tags of the generic formula $C_nF_{(2n+1)}(CR_2)_m$— include $C_6F_{13}(CH_2)_3$—, $C_6F_{13}(CH_2)_2C(CH_3)_2$—, $C_8F_{17}(CH_2)_3$—, $C_8C_{17}(CH_2)_2C(CH_3)_2$—, and $C_{10}F_{21}(CH_2)_3$—. A non-limiting example of an affinity tag of the generic formula $C_nF_{(2n-1)}(CR_2)_m$— is $CF_3CF_2(CF)_2(CF_2)_4(CH_2)_2C(CH_3)_2$—. A non-limiting example of affinity tags of the generic formula $C_nF_{(2n-3)}(CR_2)_m$— is $CF_3CF_2CC(CF_2)_4(CH_2)_2C(CH_3)_2$—.

The following formulas illustrate some non-limiting embodiments of isotopically enriched compounds with affinity tags:

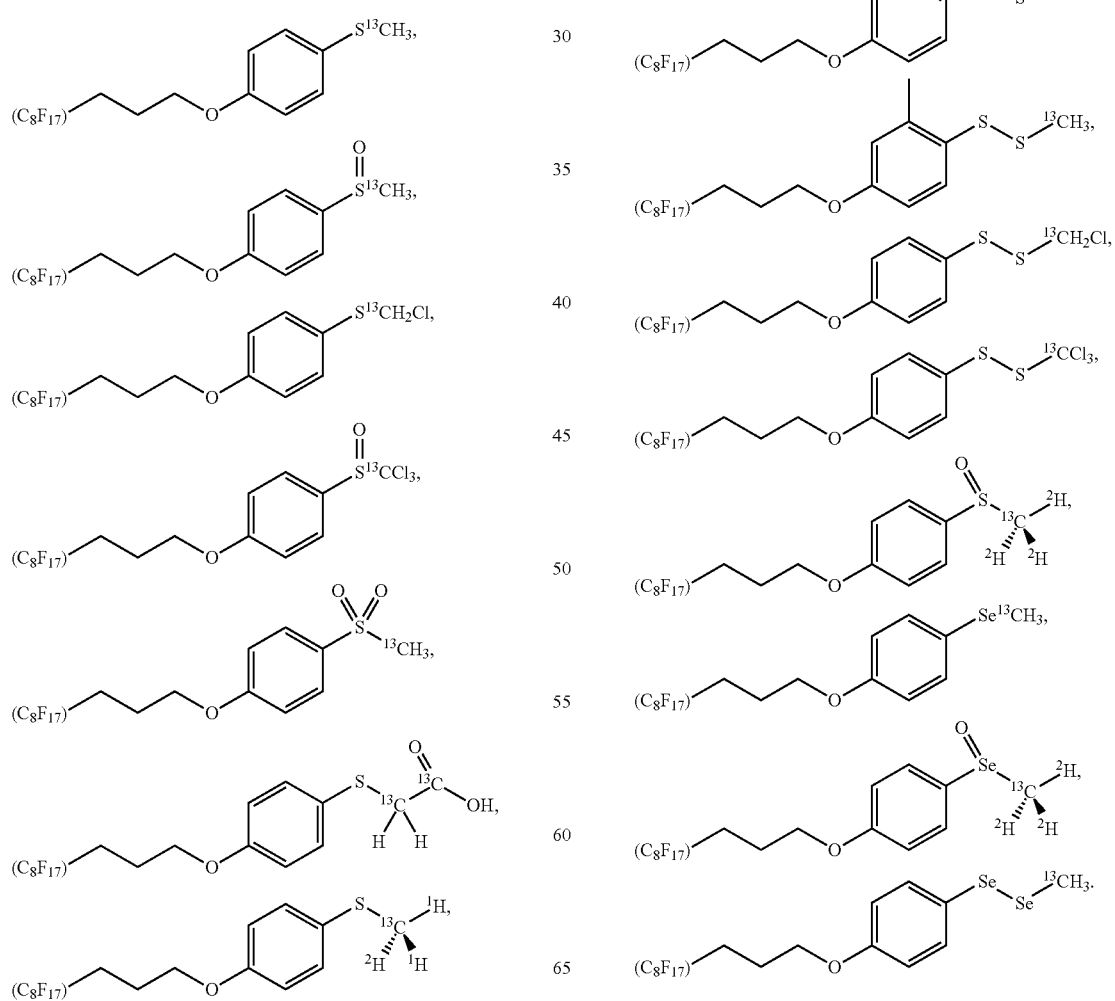

The following non-limiting EXAMPLES show a few embodiment preparations. These EXAMPLES are intended to be illustrative only because numerous modifications and variations will be apparent to those skilled in the art. Some of the EXAMPLES employ solid supports. Others employ affinity tags. Some of the materials used in the preparations were obtained from the ALDRICH CHEMICAL COMPANY in reagent quality and were used without further purification. Resin bound thiophenol (100-200 mesh, 1-1.5 millimoles/g, 1% cross-linked with divinylbenzene (DVB)) was obtained from the ALDRICH CHEMICAL COMPANY. Fluorous thiophenol (4-[3-(Perfluorooctyl)-propyl-1-oxy]thiophenol, 99+%) and FLUOROFLASH® were obtained from FLUOROUS TECHNOLOGIES INC. NMR spectra were obtained using a BRUKER DRX 300 MHz NMR spectrometer and a tunable broadband probe. $^1$H and $^{13}$C spectra were referenced to the tetramethylsilane (TMS) signal at 0.00 ppm through the NMR spectrometer's lock frequency. NMR samples were dissolved in $CDCl_3$ for those compounds soluble in organic solvents, $d_6$ benzene or expanded with $CD_2Cl_2$ for solid supported compounds. Elemental analyses were performed using a THERMO FINNIGAN FLASH 1112 series elemental analyzer. Round bottom flasks were dried with a propane torch under vacuum and cooled under argon. Reactions were performed under a positive pressure of argon, or sealed under argon when using a Falcon tube.

EXAMPLE 1

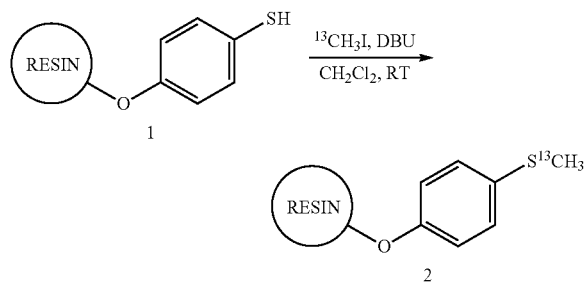

Preparation of resin bound [$^{13}$C]methyl-(4-phenol)-sulfide (2). Compound 2 was prepared as follows: Resin bound 4-thiophenol (1) (250 milligrams, about 0.312 millimoles) was added to a flame-dried round bottom flask under an argon atmosphere. Tetrahydrofuran (THF, 10 milliliters) and DBU (0.19 milliliters, 1.2 millimoles) were also added to the flask. The mixture was stirred at room temperature for 5 minutes, and then $^{13}CH_3I$ (0.059 milliliters, 0.63 millimoles) was added, and the resulting mixture was stirred overnight. The resulting resin was washed with N-methyl-2-pyrrolidone (NMP, 3×10 milliliters) and $CH_2Cl_2$ (5×10 milliliters). Analysis of the resin by NMR indicated the presence of unreacted 1. The resin was recombined with reagents with the exception that the amount of $^{13}CH_3I$ was halved. The mixture was stirred overnight. The washing steps were repeated, and the product resin was dried under a vacuum. Average loading theoretical=1.23 mmol/g, 3.94% S. Elemental Analysis: % C=87.25, % H=7.58, % S=3.45. Loading based on EA found (% S): 1.08 mmol/g (88% yield). Based on the amount of $^{13}CH_3I$ consumed, the yield of 2 was 29% (unoptimized, excess DBU consumes $^{13}CH_3I$).

EXAMPLE 2

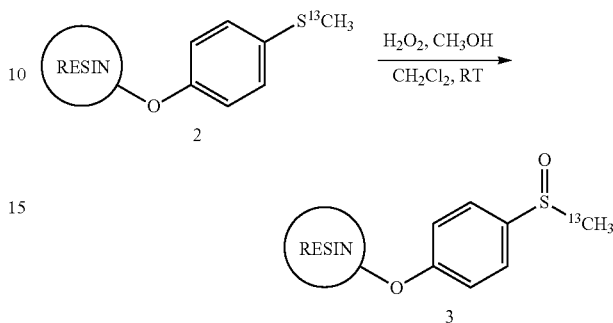

Preparation of resin bound [$^{13}$C]methyl-(4-phenol)-sulfoxide (3). Resin 3 was prepared as follows: Resin bound [$^{13}$C]methyl-(4-phenol)-sulfide (2) (200 milligrams, about 0.26 millimoles) prepared according to EXAMPLE 1, was added to a clean Falcon tube, and then $CH_2Cl_2$ (9 milliliters), methanol (1 milliliter) and hydrogen peroxide (0.059 milliliters, 0.52 millimoles) were added and the tube was sealed. The contents were mixed overnight at room temperature. Afterward, the resin was washed with methanol (3×10 milliliters), NMP (3×10 milliliters), and $CH_2Cl_2$ (5×10 milliliters). NMR analysis showed that the product included about a 1:1 mixture of 2 and 3. The product resin was combined with reactants, and the mixture was stirred overnight. After the washing steps, analysis showed that the reaction was about 90% complete. This product resin was combined with reactants and the mixture was stirred overnight again. After the washing steps, an NMR analysis showed that the reaction had gone to completion, yielding about 195 milligrams of 3. Average loading theoretical (100% yield for two steps): 1.20 mmol/g, 3.84% S. Elemental analysis: % C=85.15, % H=7.35, % S=3.75. Loading based on EA found (% S): 1.17 mmol/g (98% for two steps).

EXAMPLE 3

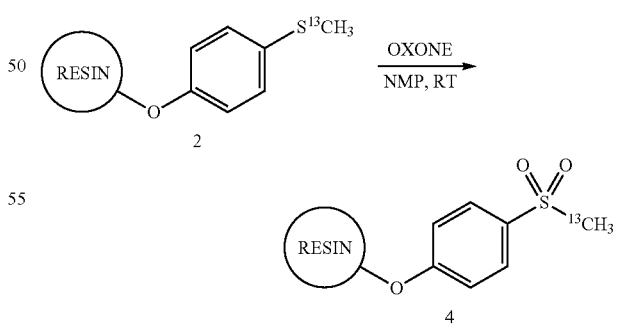

Preparation of resin bound [$^{13}$C]methyl-(4-phenol)-sulfone (4). Resin 4 was prepared as follows: Resin bound [$^{13}$C]methyl-(4-phenol)-sulfide (2) (100 milligrams, about 0.13 millimoles) prepared according to EXAMPLE 1, and N-methylpyrrolidone (NMP, 10 milliliters), were added to a clean Falcon tube. OXONE® (481 milligrams, 0.78 millimoles)

was added, the tube was sealed, and the contents were mixed overnight at room temperature. Afterward, the product resin was washed with methanol (3×10 milliliters), NMP (3×10 milliliters), and CH$_2$Cl$_2$ (5×10 milliliters). After drying under vacuum, an NMR spectrum of the product showed complete conversion to resin 4. The yield of 4 was 101 milligrams. Average loading theoretical (100% yield for two steps): 1.18 mmol/g, 3.79% S. Elemental analysis: % C=81.77, % H=7.04, % S=4.48. Loading based on EA found (% S): 1.39 mmol/g.

EXAMPLE 4

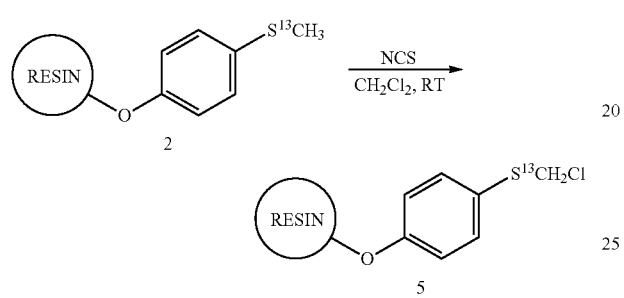

Preparation of resin bound [$^{13}$C]chloromethyl-(4-phenol)-sulfide (5). Resin 5 was prepared as follows: Resin bound [$^{13}$C]methyl-(4-phenol)-sulfide (2, 105 milligrams, about 0.13 millimoles) prepared according to EXAMPLE 1, CH$_2$Cl$_2$ (10 milliliters), and N-chlorosuccinimide (NCS, 10 milligrams, 0.075 millimoles) were added to a clean Falcon tube. After mixing the contents overnight at room temperature, the resin was washed with CH$_2$Cl$_2$ (5×10 milliliters). An NMR spectrum of the product resin showed that the product resin included about a 1:1 mixture of 2 and 5. The product resin and reactants were combined (using a smaller amount of NCS (7 milligrams, 0.052 millimoles)). After stirring for about 2 hours, the resin was washed as before. An NMR spectrum of this product resin showed that the reaction was about 90% complete. This product resin was combined with reactants using an even smaller amount of NCS (4 milligrams, 0.03 millimoles)). The mixture was stirred for about 2 hours. Afterward, the product resin was washed as before. An NMR spectrum of the product resin showed that the reaction had gone to completion. Yield: 105 milligrams of 5. Theoretical average loading: 1.18 mmol/g, 3.78% S. EA found: 68.01% C, 5.91% H, 4.22% S. Calculated loading based on found % S: 1.32 mmol/g.

EXAMPLE 5

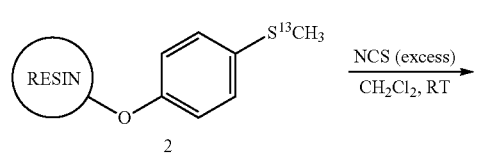

-continued

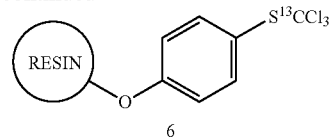

Preparation of resin bound [$^{13}$C]trichloromethyl-(4-phenol)sulfide (6). Resin 10 was prepared as follows: Resin bound [$^{13}$C]methyl-(4-phenol)-sulfide (2, 200 milligrams, about 0.26 millimoles) prepared according to EXAMPLE 1, CH$_2$Cl$_2$ (15 milliliters), and N-chlorosuccinimide (NCS, 105 milligrams, 0.78 millimoles) were added to a clean Falcon tube. The contents were mixed for two days at room temperature. The product resin was washed with CH$_2$Cl$_2$ (5×10 milliliters). An NMR spectrum of the resin showed that the reaction had gone to completion. Yield: 201 milligrams of 6. Theoretical average loading: 1.09 mmol/g, 3.49% S. EA found: 58.01% C, 4.85% H, 3.79% S. Calculated loading based on found % S: 1.18 mmol/g.

EXAMPLE 6

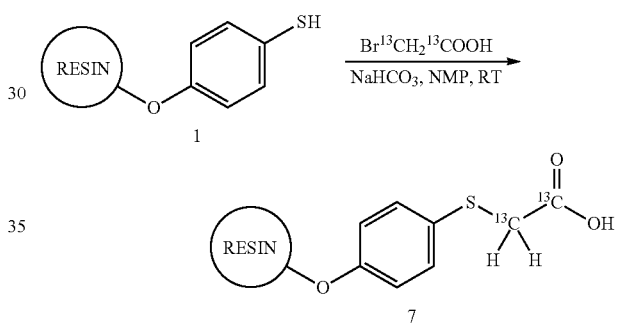

Preparation of resin bound (4-phenolsulfanyl)-[$^{13}$C$_2$]acetic acid (7). Resin 7 was prepared as: resin bound 4-thiophenol (1, 200 milligrams, about 0.25 millimoles), [$^{13}$C$_2$]bromoacetic acid (50 milligrams, 0.3 millimoles), NaHCO$_3$ (100 milligrams, 100 milligrams, 1.2 millimoles), and NMP were added to a clean Falcon tube. The tube was sealed and the contents were mixed overnight at room temperature. Afterward, the resin was washed with water (3×10 milliliters), methanol (2×10 milliliters), and CH$_2$Cl$_2$ (5×10 milliliters). After drying under vacuum, an NMR spectrum of the resin indicated good inclusion of the labeled compound into the resin. Theoretical average loading: 1.16 mmol/g, 3.71% S. EA found: 81.05% C, 6.91% H, 3.81% S. Calculated loading based on found % S: 1.19 mmol/g.

EXAMPLE 7

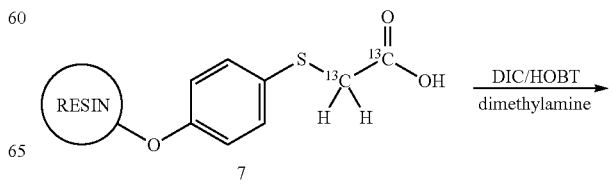

-continued

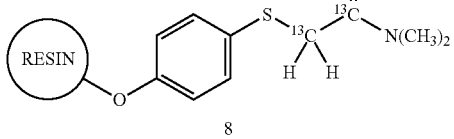

8

Preparation of resin bound (4-phenolsulfanyl)-(N,N-dimethyl)-[$^{13}C_2$]acetamide (8). Resin 8 was prepared as follows: resin bound (4-phenolsulfanyl)-[$^{13}C_2$]acetic acid (7, 200 milligrams, about 1.23 millimoles) prepared according to EXAMPLE 6 was added to a clean Falcon tube along with 1-hydroxybenzotriazole (HOBT, 0.5 M in NMP, 0.54 milliliters, 0.27 millimoles), and N,N-diisopropylcarbodiimide (DIC, 42 μl, 0.27 millimoles). Dimethylamine (2 M in THF, 0.27 milliliters, 0.54 millimoles) was then added along with $CH_2Cl_2$ (10 milliliters). The tube was sealed and the contents were mixed overnight at room temperature. The resin was washed with $CH_2Cl_2$ (5×10 milliliters) and dried under vacuum. An NMR spectrum of the resin showed that the reaction was not complete. The product resin from the incomplete reaction was combined with fresh reactants and mixed at room temperature overnight. Washing was repeated as before, and the NMR spectrum of the resin indicated that the reaction was about 90% complete. This resin was combined with reagents and mixed overnight at room temperature. After washing, the NMR spectrum of the resin indicated that the reaction was complete. Theoretical average loading: 1.12 mmol/g, 3.58% S. EA found: 79.16% C, 6.97% H, 3.24% S. Calculated loading based on found % S: 1.01 mmol/g (~91% for two steps).

EXAMPLE 8

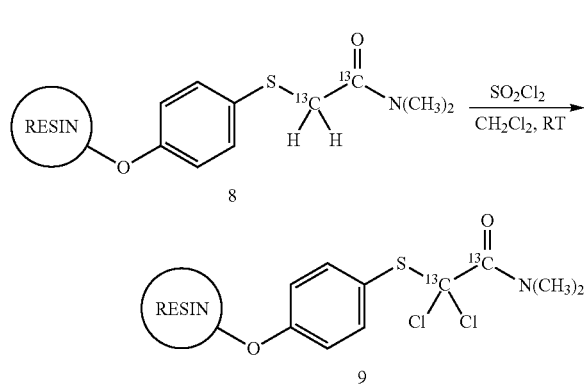

Preparation of resin bound (4-phenolsulfanyl)-(N,N-dimethyl)-[$^{13}C_2$]dichloroacetamide (9). Resin 9 was prepared as follows: resin bound (4-phenolsulfanyl)-(N,N-dimethyl)-[$^{13}C_2$]acetamide (8, 400 milligrams, about 0.45 millimoles) prepared according to EXAMPLE 7, and $CH_2Cl_2$ (15 milliliters) were added to a clean Falcon tube. $SO_2Cl_2$ (0.11 milliliters, 1.35 millimoles) was added, the tube was sealed, and the contents were mixed at room temperature for about 2 hours. Afterward, the resin was washed with $CH_2Cl_2$ (5×10 milliliters) and dried under vacuum. An NMR spectrum of the resin indicated that the reaction was complete. Theoretical average loading: 1.04 mmol/g, 3.34% S. EA found: 68.18% C, 5.67% H, 3.42% S. Calculated loading based on found % S: 1.06 mmol/g.

EXAMPLE 9

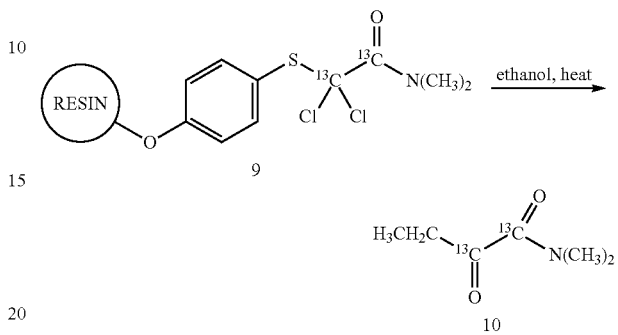

Preparation of N,N-dimethyl-[$^{13}C_2$]oxalamic acid ethyl ester (10). Compound 10 was prepared as follows: resin bound (4-phenolsulfanyl)-(N,N-dimethyl)-[$^{13}C_2$]dichloroacetamide (9, 400 milligrams, about 0.42 millimoles), water (0.25 milliliters), and ethanol (15 milliliters) were added to a round bottom flask. The mixture was heated to a temperature of about 80 degrees Celsius overnight. After filtering away the resin, the filtrate was evaporated to give a yellow oil (57 milligrams, essentially quantitative yield). An NMR spectrum of the oil indicated that the oil was 10 in high purity.

EXAMPLE 10

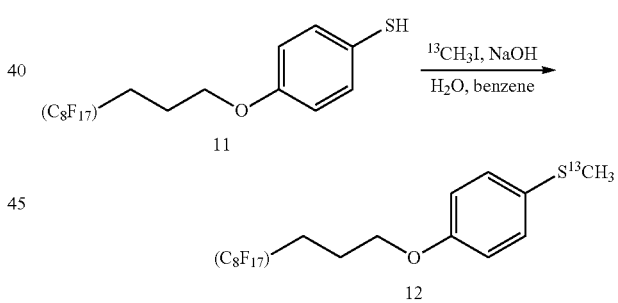

Preparation of [$^{13}C$]methyl sulfide, 4-[3-($C_8F_{17}$)$C_3H_6$-1-O]$C_6H_4S^{13}CH_3$ (12). Compound 12 was prepared as follows: 4-[3-perfluorooctyl)-propyl-1-oxy]thiophenol (11, 500 milligrams, 0.85 millimoles) and NaOH (100 milligrams, 2.6 millimoles) were added under an argon atmosphere to a flame dried round bottom flask. Benzene (7.5 milliliters) was then added, followed by water (0.85 milliliters). After stirring at room temperature for about five minutes, $^{13}CH_3I$ (0.12 milliliters, 1.28 millimoles) was added and the reaction was monitored by NMR spectroscopy. After about two hours, the signal due to the starting material $^{13}CH_3I$ had an intensity that was about equal to the intensity of the signal due to the $^{13}C$ of product compound (12). After about twenty-four hours, only minor intensity changes corresponding to slight evaporation of the $^{13}CH_3I$ were observed. The reaction mixture was diluted with water and the aqueous layer was extracted with $CH_2Cl_2$. The organic portion was dried using $Na_2SO_4$, filtered, and evaporated to give a white powder. An NMR spectrum of the product showed only small amounts of impurities. The material was purified by preparative thin layer chromatography (12% ethyl acetate in hexanes) to give 492 milligrams (96% yield, 64% based on $^{13}CH_3I$) of 12 as a white powder.

EXAMPLE 11

Preparation of [$^{13}C$]methyl sulfide, 4-[3-($C_8F_{17}$)$C_3H_6$-1-O]$C_6H_4S^{13}CH_3$ (12). Compound 12 was prepared as follows: 4-[3-perfluorooctyl)-propyl-1-oxy]thiophenol (11, 100 milligrams, 0.17 millimoles) was combined with benzene (3 milliliters), 1,8-diazabicyclo[5.4.0.]undec-7-ene (DBU, 0.101 milliliters, 0.68 millimoles) and $^{13}CH_3I$ (0.032 milliliters, 0.34 millimoles) under an argon atmosphere at room temperature. After about one hour, no $^{13}CH_3I$ was visible by $^{13}C$ NMR spectroscopy. The reaction mixture was diluted with water and the aqueous layer was extracted with $CH_2Cl_2$. The organic portion was dried over $Na_2SO_4$, filtered, and evaporated to give a white powder. The crude material was purified by preparative thin layer chromatography (12% ethyl acetate in hexanes) to give 86 milligrams (85% yield) of 12 as a white powder.

EXAMPLE 12

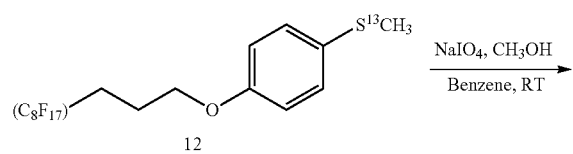

Preparation of [$^{13}C$]methyl sulfoxide, 4-[3-($C_8F_{17}$)$C_3H_6$-1-O]$C_6H_4SO^{13}CH_3$ (13). Compound 13 was prepared as follows: A solution of [$^{13}C$]methyl sulfide, 4-[3-($C_8F_{17}$)$C_3H_6$-1-O]$C_6H_4S^{13}CH_3$ (12, 150 milligrams, 0.25 millimoles) in benzene (2 milliliters) was prepared and then added to a solution of $NaIO_4$ (53 milligrams, 0.25 millimoles) in methanol (4 milliliters). The reaction mixture was stirred at room temperature and monitored by NMR spectroscopy. After about 48 hours, only trace amounts of compound 12 were visible by $^{13}C$ NMR. The mixture was diluted with water and extracted with $CH_2Cl_2$. The organic portion was dried over $Na_2SO_4$, filtered, and evaporated to give a white powder. Purification by preparative thin layer chromatography (1:1 ethyl acetate:hexanes) gave 144 milligrams (93% yield) of 13 as a white powder.

EXAMPLE 13

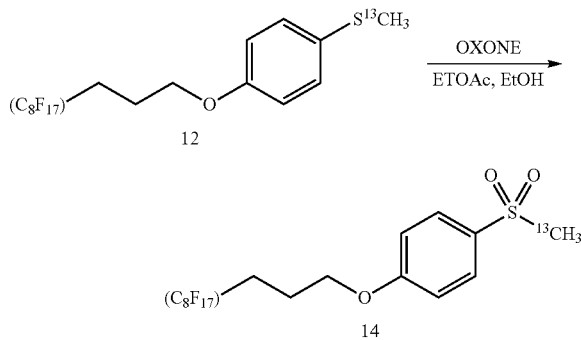

Preparation of [$^{13}C$]methyl sulfone, 4-[3-($C_8F_{17}$)$C_3H_6$-1-O]$C_6H_4SO_2{}^{13}CH_3$ (14). Compound 14 was prepared as follows: A solution of [$^{13}C$]methyl sulfide, 4-[3-($C_8F_{17}$)$C_3H_6$-1-O]$C_6H_4S^{13}CH_3$ (12, 150 milligrams, 0.25 millimoles) in a 1:1 solvent mixture of ethyl acetate:ethanol (3 milliliters) was prepared. The solution was added to a solution of OXONE™ (460 milligrams, 0.75 millimoles) in water (13 milliliters). The mixture was stirred at room temperature and monitored by thin layer chromatography (1:1 ethyl acetate:hexanes) and by NMR spectroscopy. The reaction was quenched after about 48 hours by dilution with water. The organic portion was extracted with $CH_2Cl_2$, dried using $Na_2SO_4$, filtered, and evaporated to give a white powder. Purification by preparative thin layer chromatography (1:1 ethyl acetate:hexanes) yielded 143 milligrams (91% yield) of 14 as a white powder.

EXAMPLE 14

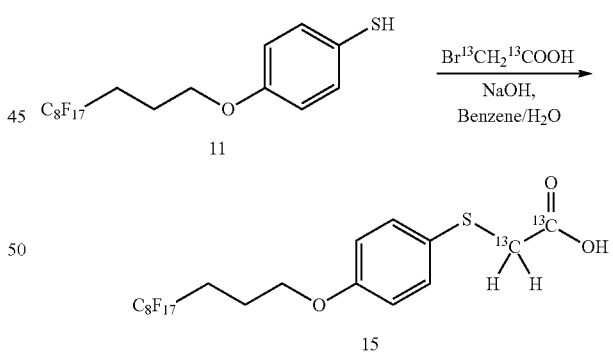

Preparation of Perfluorooctyl-propyl-(4-phenolsulfanyl)-[$^{13}C_2$]acetic acid (15). Compound 15 was prepared as follows: A clear solution of compound 11 (500 milligrams, 0.85 millimoles) in benzene (6 milliliters) was prepared under argon. A solution of sodium hydroxide (100 milligrams, 2.6 millimoles) in water (0.8 milliliters) was also prepared and added with stirring to the solution of compound 11, after which the clear solution turned white and became chunky and frothy. A solution of bromoacetic acid [$^{13}C_2$] in benzene (2 milliliters) was also prepared and added to the white mixture. The resulting mixture was stirred to 1 hour, after which it became a uniform white/cream colored suspension. The mixture was stirred an additional 24 hours, then quenched with saturated NH₄Cl. After rinsing the aqueous layer with CH₂Cl₂, the aqueous layer was acidified with 6 N HCl to pH 2. Extraction with CH₂Cl₂ followed by drying (Na₂SO₄) and evaporation of the combined organics gave compound 15 (426 milligrams, 78% yield) in good purity as a white powder. The product was used without further purification in subsequent reactions. Elemental analysis calculated: 35.61% C, 2.03% H, 4.96% S. Found: 34.97% C, 1.96% H, 4.16% S.

EXAMPLE 15

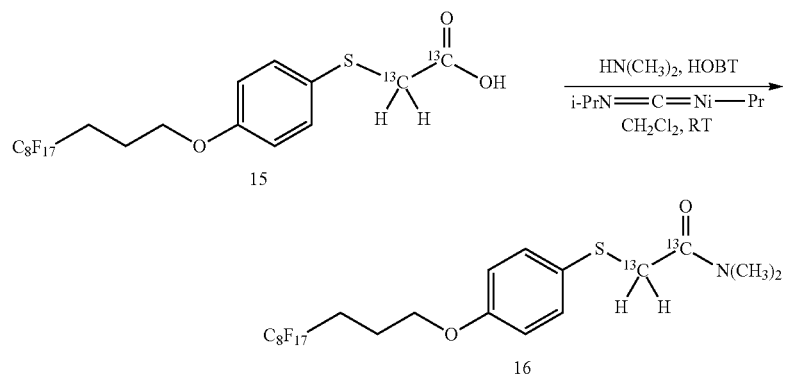

Preparation of (Perfluorooctyl)-propyl-(4-phenolsulfanyl)-(N,N-dimethyl)-[$^{13}C_2$]acetamide (16). Compound 16 was prepared as follows: A solution of compound 15 in (10 milliliters) was prepared. A 0.5 M (molar) solution of 1-hydroxybenzotriazole (HOBT, 0.4 milliliters, 0.21 millimoles) in N-methylpyrrolidone was added, followed by addition of diisopropylcarbodiimide (0.033 milliliters, 0.21 millimoles). The resulting mixture was stirred at room temperature under argon. Five minutes later, a 2 M solution of HN(CH₃)₂ (0.2 milliliters, 0.42 millimoles) in tetrahydrofuran (THF) was added and the reaction mixture was stirred overnight. After NMR analysis confirmed the reaction was complete, the solvent was evaporated and the residue was dissolved in a minimum amount of N,N-dimethylformamide (DMF). The resulting mixture was eluted through a FLUOROFLASH® SPE cartridge, using 80:20 methanol:H₂O to wash and 100% methanol to elute the product. After evaporation of the product fraction, compound 16 (113 milligrams, 95% yield) was obtained as a white powder. Elemental analysis calculated: 2.08% N, 37.75% C, 2.69% H, 4.67% S. Found: 2.32% N, 36.69% C, 2.96% H, 2.75% S.

EXAMPLE 16

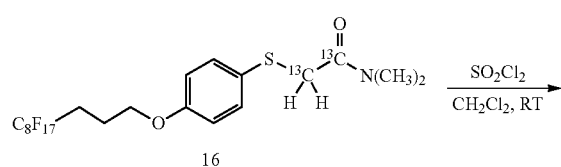

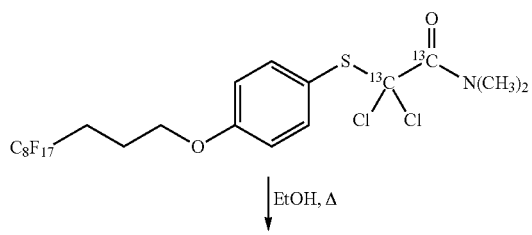

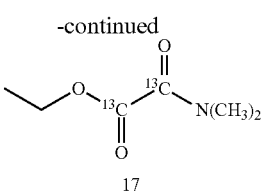

Preparation of N,N-Dimethyl-[$^{13}C_2$]oxalamic acid ethyl ester (17). Compound 17 was prepared as follows: A solution of compound 16 (375 milligrams, 0.56 millimoles) in CH₂Cl₂ (15 milliliters) was prepared under argon. The solution was chilled to zero degrees Celsius and SO₂Cl₂ (0.14 milliliters, 1.7 millimoles) was added. The mixture was stirred at zero degrees Celsius for 3 hours. After NMR verification of reaction completion, the solvent was evaporated and the residue was taken up in ethanol (9.5 milliliters) and water (0.5 milliliters). The mixture was heated to 70 degrees Celsius, during which the white solid dissolved. The mixture was heated at this temperature overnight. Afterward, the mixture was cooled, and diluted with water, and eluted through a FLUOROFLASH® SPE cartridge, using 80:20 methanol:H₂O to elute the amide ester product and 100% methanol to elute the fluorous supported thiol. NMR analysis was positive for pure compound 17 (76 milligrams, 93% yield), as well as thiol (303 milligrams, 92% recovery). The efficacy of the thiol was tested on a subsequent reaction that gave an addition product in better than 85% yield.

In summary, isotopically labeled compounds are prepared using compositions having solid phase supports or affinity tags. Chemical detachment of the support or tag results in a labeled compound. The reactions can be monitored easily using NMR spectroscopy, and the support can be regenerated.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for synthesizing an isotopically enriched compound, comprising:
    forming a composition comprised of the formula

A-D-E-C(TXZ)

wherein A is a support selected from the group consisting of a polymer support, a resin support, a metal support, a nanoparticle support, a magnetic bead support, a silica support, a silicon support, a glass support, a ceramic support, and a core-shell compound support;
    wherein D comprises aryl having 6-10 ring atoms and an oxygen atom attached to A;
    wherein E is selected from the group consisting of sulfur, sulfoxide, sulfone, selenium, selenoxide, or selenone;
    wherein T, X, and Z comprise groups each independently chosen from $^1$H, $^2$H, a $C_1$-$C_4$ alkyl, fluoro, chloro, bromo, iodo, amino, NHR, $NR_2$, and OR;
    wherein R comprises $C_1$-$C_4$ alkyl, chloro, bromo, amino, a monocyclic aryl, substituted monocyclic aryl, bicyclic aryl, and substituted bicyclic aryl; and
    wherein at least one of C, T, X, and Z groups comprises a stable isotope, wherein the stable isotope of C is $^{13}$C and wherein the stable isotope of T, X, Z comprises $^{13}$C or $^2$H; and
    subjecting the composition to conditions whereby —C(TXZ) detaches from E and becomes part of an isotopically labeled compound.

2. The method of claim 1, wherein aryl having an oxygen of D comprises monocyclic aryloxy, functionalized monocyclic aryloxy, bicyclic aryloxy, functionalized bicyclic aryloxy,
    wherein functionalized monocyclic aryloxy, and functionalized bicyclic aryloxy comprise a substituent chosen from alkyl, haloalkyl, cycloalkyl, halo, nitro, cyano, —OM, and —COOQ, wherein M is chosen from hydrogen, alkyl, haloalkyl, cycloalkyl, phenyl, and substituted phenyl, and wherein Q is chosen from hydrogen and alkyl.

3. The method of claim 1, wherein E is sulfur, sulfoxide, or sulfone; wherein C is $^{13}$C; and wherein at least one of T, X, and Z is $^2$H.

4. The method of claim 1, wherein haloalkyl comprises fluoroalkyl, bromoalkyl, chloroalkyl, and iodoalkyl.

5. The method of claim 1, wherein T, X, and Z comprise monocyclic aryl, monocyclic aryloxy, functionalized monocyclic aryloxy, bicyclic aryl, bicyclic aryloxy, functionalized bicyclic aryloxy,
    wherein functionalized monocyclic aryl, functionalized monocyclic aryloxy, functionalized bicyclic aryl, and functionalized bicyclic aryloxy comprise a substituent chosen from alkyl, haloalkyl, cycloalkyl, halo, nitro, cyano, —OM, and —COOQ, wherein M is chosen from hydrogen, alkyl, haloalkyl, cycloalkyl, phenyl, and substituted phenyl, and wherein Q is chosen from hydrogen and alkyl.

6. The method of claim 1, wherein said resin support is selected from polystyrene and resin-bound thiophenol crosslinked with divinylbenzene.

7. The method of claim 1 wherein group D is 1,4-disubstituted aryl having an oxygen attached to group A, wherein group E is selected from sulfur, sulfoxide, and sulfone.

* * * * *